United States Patent [19]

Bredesen et al.

[11] Patent Number: 5,213,108
[45] Date of Patent: May 25, 1993

[54] VISUAL DISPLAY STETHOSCOPE

[75] Inventors: Mark S. Bredesen; Elliot D. Schmerler, both of Incline Village, Nev.

[73] Assignee: Blood Line Technology, Inc., Incline Village, Nev.

[21] Appl. No.: 782,079

[22] Filed: Oct. 24, 1991

Related U.S. Application Data

[63] Continuation-in-part of Ser. No. 628,482, Dec. 17, 1990, which is a continuation of Ser. No. 153,719, Feb. 4, 1988, Pat. No. 5,010,889.

[51] Int. Cl.$^5$ .......................... A61B 5/02; A61B 7/04
[52] U.S. Cl. ..................................... 128/715; 128/773; 381/67
[58] Field of Search ............... 128/773, 695, 696, 700, 128/710, 715; 181/126, 130, 131; 381/67

[56] References Cited

U.S. PATENT DOCUMENTS

| | | |
|---|---|---|
| 3,858,005 | 12/1974 | Marshall et al. |
| 3,985,121 | 10/1976 | Hallenbrand |
| 4,170,717 | 6/1977 | Walshe |
| 4,226,248 | 10/1980 | Minolli |
| 4,270,547 | 6/1981 | Steffan et al. |
| 4,362,164 | 12/1982 | Little et al. |
| 4,396,018 | 8/1983 | Sibley |
| 4,417,306 | 11/1983 | Citron et al. |
| 4,422,458 | 12/1983 | Krabeth |
| 4,459,993 | 7/1984 | Foreman |
| 4,483,346 | 11/1984 | Slaven |
| 4,528,689 | 7/1985 | Katz |
| 4,537,202 | 8/1985 | Mancini et al. |
| 4,549,551 | 10/1985 | Dyck et al. |
| 4,586,514 | 5/1986 | Schlagger et al. |
| 4,624,163 | 11/1986 | Slaven |
| 4,635,645 | 1/1987 | Fucashuma |
| 4,649,930 | 3/1987 | Groetsch |
| 4,672,977 | 6/1987 | Kroll |
| 4,679,570 | 7/1987 | Lund et al. |
| 4,712,565 | 12/1987 | Katz et al. |
| 4,719,923 | 1/1988 | Hartwell et al. |
| 4,720,866 | 1/1988 | Elias et al. |
| 4,770,189 | 9/1988 | Shyu |
| 5,010,889 | 4/1991 | Bredesen et al. |
| 5,025,809 | 6/1991 | Johnson et al. |

FOREIGN PATENT DOCUMENTS

WO89/06932 8/1989 PCT Int'l Appl.
WO90/08503 8/1990 PCT Int'l Appl.

OTHER PUBLICATIONS

EP 89 90 2573 European Search Report.
HP Sonos 1000 Cardiovascular Imaging System, Technical Data, Copyright date of 1991.
HP Sonos 1000 Comprehensive Cardiac Analysis Function, Technical Data, Copyright date of 1990.
8813A Heart Sound Amplifier, Principles of Operation, from Hewlett Packard, no date.
Medical and Biological Engineering and Computing, vol. 18, No. 1, Jan. 1980, pp. 19-26, to Iwata et al. entitled, "Algorithm for detecting the first and the second heart sounds by spectraltracking".
Medical and Biological Engineering and Computing, vol. 15, No. 4, Jul. 1977, pp. 407-412, to Iwata et al., entitled: "Pattern classification of the phonocardiogram using linear prediction analysis".

Primary Examiner—William E. Kamm
Assistant Examiner—John P. Lacyk
Attorney, Agent, or Firm—Merchant, Gould, Smith, Edell, Welter & Schmidt

[57] ABSTRACT

An visual display stethoscope for use in the auscultation of body sounds is disclosed. The stethoscope is adapted for display, manipulation and analysis of the received body sounds. The present invention includes a stethoscope electronically coupled to a display module. The display module has the ability to display an analog representation of the received body sounds and includes menu keys for selecting among the various functions provided by the stethoscope for manipulation and analysis of the waveform data. These functions include real time analog filtering of displayed waveforms, digital filtering of stored waveforms, and interval timing between strategic positions in the body sound waveforms. The visual display stethoscope therefore is of significant aid to physicians in the analysis, recognition, and diagnosis of abnormalities which can be examined via auscultation methods.

35 Claims, 34 Drawing Sheets

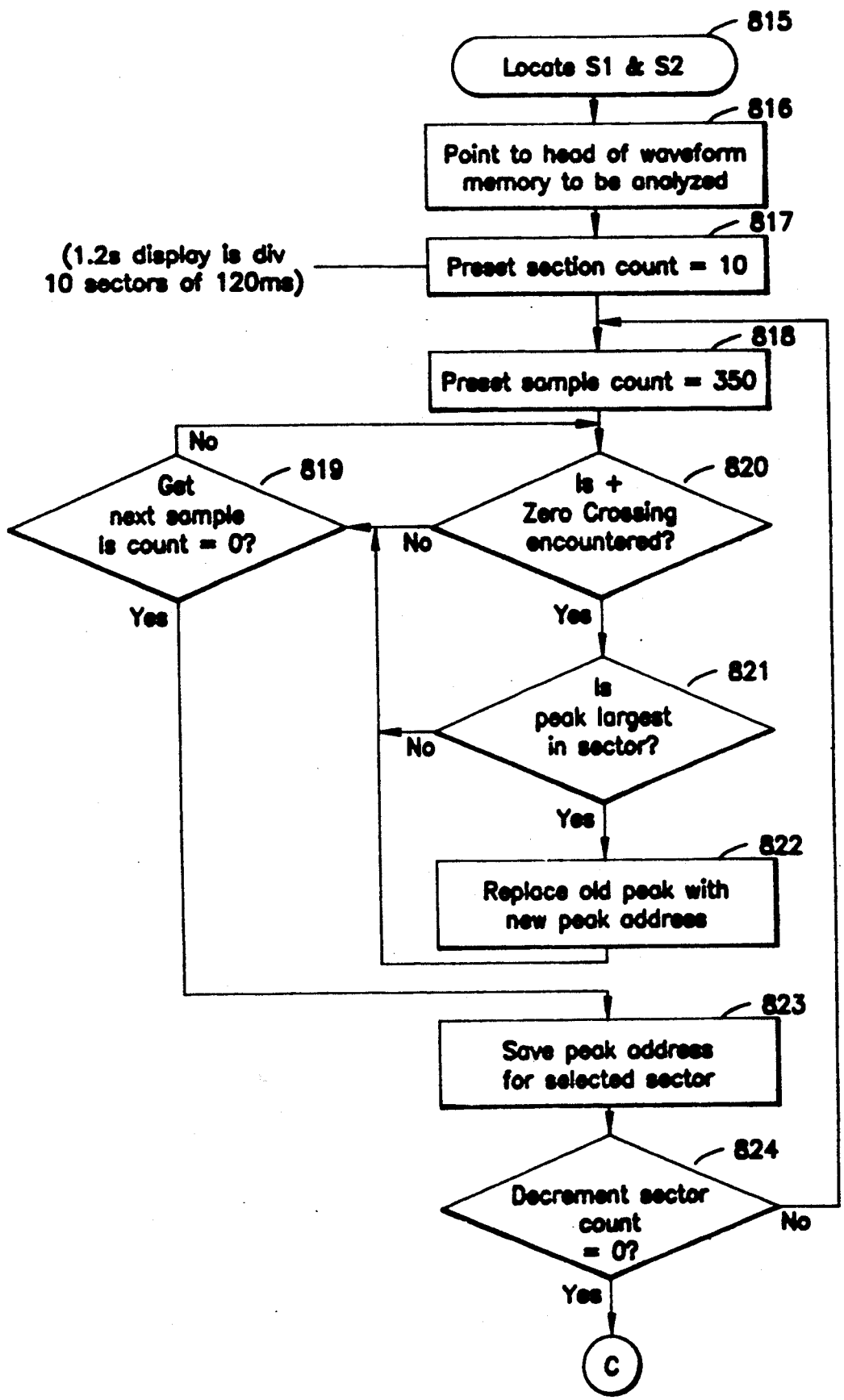
FIG. 8B (To FIG. 8C)

|     | A | B | C | D | E | F |
|-----|---|---|---|---|---|---|
| PMI | X |   |   |   |   |   |
| 1 | Y | Y | Y | Y | Y | Y |
| 2 | Y | Y | Y | Y | Y | Y |
| 3 | Y | Y | Y | Y | Y | Y |
| 4 | Y | Y | Y | Y | Y | Y |
| 5 | Y | N/Y | N/Y | N/Y | N/Y | N/Y |
| 6 | N | N | N | N | N | N |
| 7 | N/Y | N/Y | N/Y | N/Y | N | N |
| 8 | N/Y | N/Y | N/Y | N/Y | N/Y | N/Y |

FIG. 9A

|     | A | B | C | D | E | F |
|-----|---|---|---|---|---|---|
| PMI |   |   | X |   |   |   |
| 1 | Y | Y | Y | Y | Y | Y |
| 2 | Y | Y | Y | Y | Y | Y |
| 3 | Y | Y | Y | Y | Y | Y |
| 4 | Y | Y | Y | Y | Y | Y |
| 5 | N | N | N | N | N | N |
| 6 | N/Y | N/Y | Y | N/Y | N/Y | N/Y |
| 7 | N/Y | N/Y | N/Y | N/Y | N | N |
| 8 | N/Y | N/Y | N/Y | N/Y | N/Y | N/Y |

FIG. 9B

|     | A | B | C | D | E | F |
|-----|---|---|---|---|---|---|
| PMI |   |   |   |   |   | X |
| 1 | Y | Y | Y | Y | Y | Y |
| 2 | Y | Y | Y | Y | Y | Y |
| 3 | Y | Y | Y | Y | Y | Y |
| 4 | N/Y | N/Y | N/Y | N/Y | N/Y | N/Y |
| 5 | N/Y | N/Y | N/Y | N/Y | N/Y | Y |
| 6 | N | N | N | N | N | N |
| 7 | N/Y | N/Y | N/Y | N/Y | N/Y | N/Y |
| 8 | N/Y | N/Y | N/Y | N/Y | N/Y | N/Y |

FIG. 9C

|     | A | B | C | D | E | F |
|-----|---|---|---|---|---|---|
| PMI |   |   |   |   | X |   |
| 1 | Y | Y | Y | Y | Y | Y |
| 2 | Y | Y | Y | Y | Y | Y |
| 3 | Y | Y | Y | Y | Y | Y |
| 4 | Y | Y | Y | Y | Y | Y |
| 5 | N | N | N | N | N | N |
| 6 | N/Y | N/Y | N/Y | N/Y | Y | N/Y |
| 7 | N/Y | N/Y | N/Y | N/Y | N/Y | N/Y |
| 8 | N/Y | N/Y | N/Y | N/Y | N/Y | N/Y |

FIG. 9D

|   | A | B | C | D | E | F |
|---|---|---|---|---|---|---|
| 1 | Y | Y | Y | Y | Y | Y |
| 2 | N | N | N | N | N | N |
| 3 | N | N | N | N | N | N |
| 4 | N | N | N | N | N | N |
| 5 | N | N | N | N | N | N |
| 6 | 50 | 50 | 50 | 50 | 50 | 50 |

|   | A | B | C | D | E | F |
|---|---|---|---|---|---|---|
| 1 | Y | Y | Y | Y | Y | N |
| 2 | N | N | N | N | N | Y |
| 3 | N | N | N | N | N | N |
| 4 | N | N | N | N | N | N |
| 5 | N | N | N | N | N | N |
| 6 | 50 | 50 | 50 | 50 | 50 | 50 |

VISUAL DISPLAY STETHOSCOPE

CROSS REFERENCE TO RELATED APPLICATION

This patent application is a continuation-in-part of U.S. patent application Ser. No. 07/628,482, filed Dec. 17, 1990, which is a continuation of U.S. patent application Ser. No. 07/153,719, filed Feb. 4, 1988, now U.S. Pat. No. 5,010,889, the latter of which is incorporated herein by reference.

FIELD OF THE INVENTION

The present invention relates to diagnostic auscultation and in particular to an electronic stethoscope for display and analysis of sounds made by the various body structures.

BACKGROUND OF THE INVENTION

Analysis of heart, lung and vascular disorders by means of noninvasive auscultation has long been a very useful tool for medical diagnosis of ailments. By using a stethoscope, a physician would listen to the heart sounds, chest sounds or other body sounds to identify sounds associated with abnormalities. The most common of these are heart murmurs which, when identified, indicate specific abnormalities in the functioning of the heart. However, identifying specific murmurs, like identifying heart sounds, is difficult. Developing the skill to make a proper analysis takes years of study and practice. Acquiring expertise in identifying heart sounds and murmurs takes experience that many physicians do not have the opportunity to acquire, since many heart murmurs are very rare and are seldom encountered by general practitioners.

In addition, most of these body sounds fall either just at or below the audible frequency range of the human ear. This makes proper diagnosis extremely difficult for general practitioners and experts alike.

Due to the rarity of many heart murmurs and other body sounds, and because they often fall in the sub-audible range of the human ear, recognition and correct diagnosis of such sounds from listening directly to the body sounds is difficult or impossible for the inexperienced physician. Hence, there is a need in the medical arts for automatic display, measurement and manipulation of detected body sounds for aiding medical practitioners in the analysis and diagnosis of abnormalities. Thus, for a physician who desires to diagnose a condition from a visual display of body sounds, there is a need in the medical arts to provide a mechanism for a physician to precisely measure and study a variety of waveform features in a display of body sounds.

SUMMARY OF THE INVENTION

A visual display stethoscope method and apparatus for performing auscultation and for automatically displaying the body sounds is described in which the body sounds are received, digitized and stored in a memory. The body sounds may be recorded from a plurality of locations on the body. The visual display stethoscope allows precise timing measurements, digital and analog filtering, and other phonocardiogram manipulations to be made for aiding the medical practitioner in the analysis of abnormalities.

The apparatus and method for using the present invention for auscultation is described as applicable to heart sounds, lung sounds, bruits, and other body sounds. The apparatus includes an LCD display which is capable of displaying along a linear time axis the analog view of the recorded body sound. The display also prompts the user as to the use of the device. The apparatus includes a keypad by which the operator controls the functions of the device. The apparatus also includes a mechanism for a physician to precisely measure and study a variety of waveform features in a display of body sounds. The apparatus further includes a mechanism for performing real time analog filtering of the displayed waveform, and digital post capture filtering on stored waveforms.

BRIEF DESCRIPTION OF THE DRAWINGS

In the drawings, where like numerals refer to like components throughout the several views.

FIGS. 3a-3i comprise the detailed electrical schematic diagrams of the microprocessor-based visual display stethoscope, and are to be viewed together;

FIGS. 4a-4f are software flow charts representing the operational flow of the visual display stethoscope;

DETAILED DESCRIPTION OF THE PREFERRED EMBODIMENT

In the following detailed description of the preferred embodiment, reference is made to the accompanying drawings which form a part hereof, and in which is shown by way of illustration a specific embodiment in which the invention may be practiced. This embodiment is described in sufficient detail to enable those skilled in the art to practice the invention, and it is to be understood that other embodiments may be utilized and that structural changes may be made without departing from the scope of the present invention. The following detailed description is, therefore, not to be taken in a limiting sense, and the scope of the present invention is defined by the appended claims.

Figure 1:
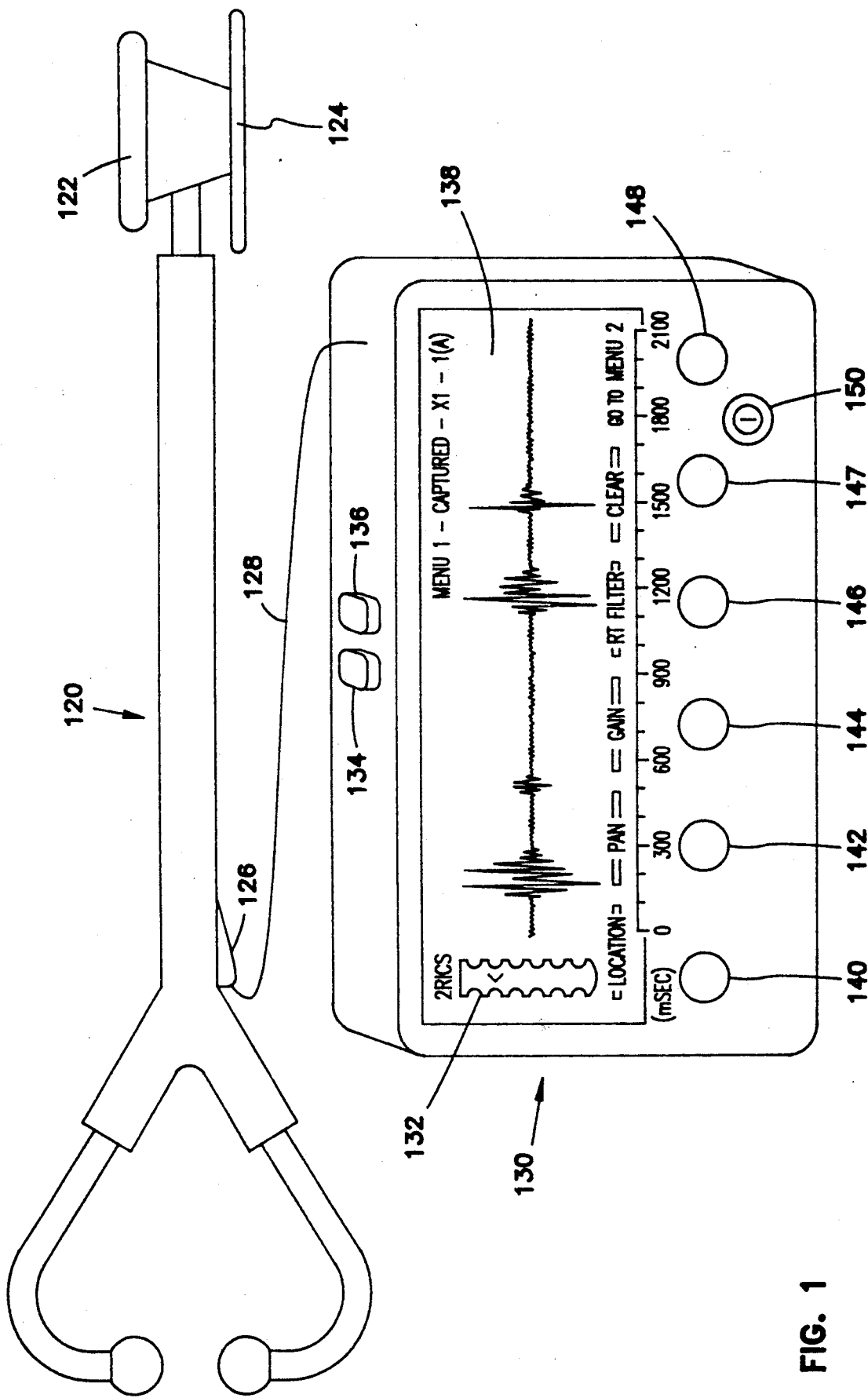
FIG. 1 is a pictorial view of the apparatus implementing the preferred embodiment of the present invention.

Referring to FIG. 1, the preferred embodiment of the present invention looks like other conventional stethoscopes, having a stethoscope 120 with the addition of a separate electronic display module 130. The instrument consists of a conventional stethoscope bell 122 acoustically coupled to an electronic interface. The audio signals are processed and digitized via a sampled analog to digital waveform acquisition procedure. The digitized audio is stored in data base memory for further analysis, while simultaneously being displayed on the LCD graphic display 138. A transducer 124 converts body sounds to electrical signals and resides in stethoscope bell 122. Bell 122 also has an acoustic input therein. The transducer 124 is operatively coupled by electrical connection to the display module 130 via a jack 126 in stethoscope 120 and electrically conductive cord 128.

Presently, transducer 124 can have the same performance characteristics as that described for miniature microphone 225 described below in Hardware Description.

Display module 130 has a liquid crystal graphic display 138 and at least one and preferably a number of menu keys 140-148 and an on/off switch 150 on a front surface for use by a physician.

Display module 130 preferably has two switches electrically coupled to transducer 124 to control electrical signals from the transducer 124 and to capture and store at least one electrical signal as a waveform of body sounds for visual representation, measurement, and study on display module 130. Operation of these switches can be varied as desired. Presently, pressing sweep switch 134 once activates electronics of the visual display stethoscope and initiates the software sequences shown in FIG. 4. Pressing sweep switch 134 again causes a continuous display of a visual representation of body sounds as waveforms on LCD graphic display 138. Thereafter releasing sweep switch 134 captures into temporary memory 221 electrical signals displayed as waveforms and the waveforms immediately preceding in the displayed waveforms. Pressing save switch 136 enters the captured electrical signals into permanent memory 219.

Menu keys 140-148 are the means through which a user selects among the various functions provided by the visual display stethoscope of the present invention. There is also a peripheral data port (not shown) which is used for the transfer of data base memory to a digital plotter, and/or storage in a larger memory media. The system is powered from rechargeable batteries, and controlled by an intelligent power control system. If left unattended, the system will shut itself off while still retaining data base memory. There also exists a low battery detection circuit which will alert the user of that condition.

Hardware Description

Figure 2:
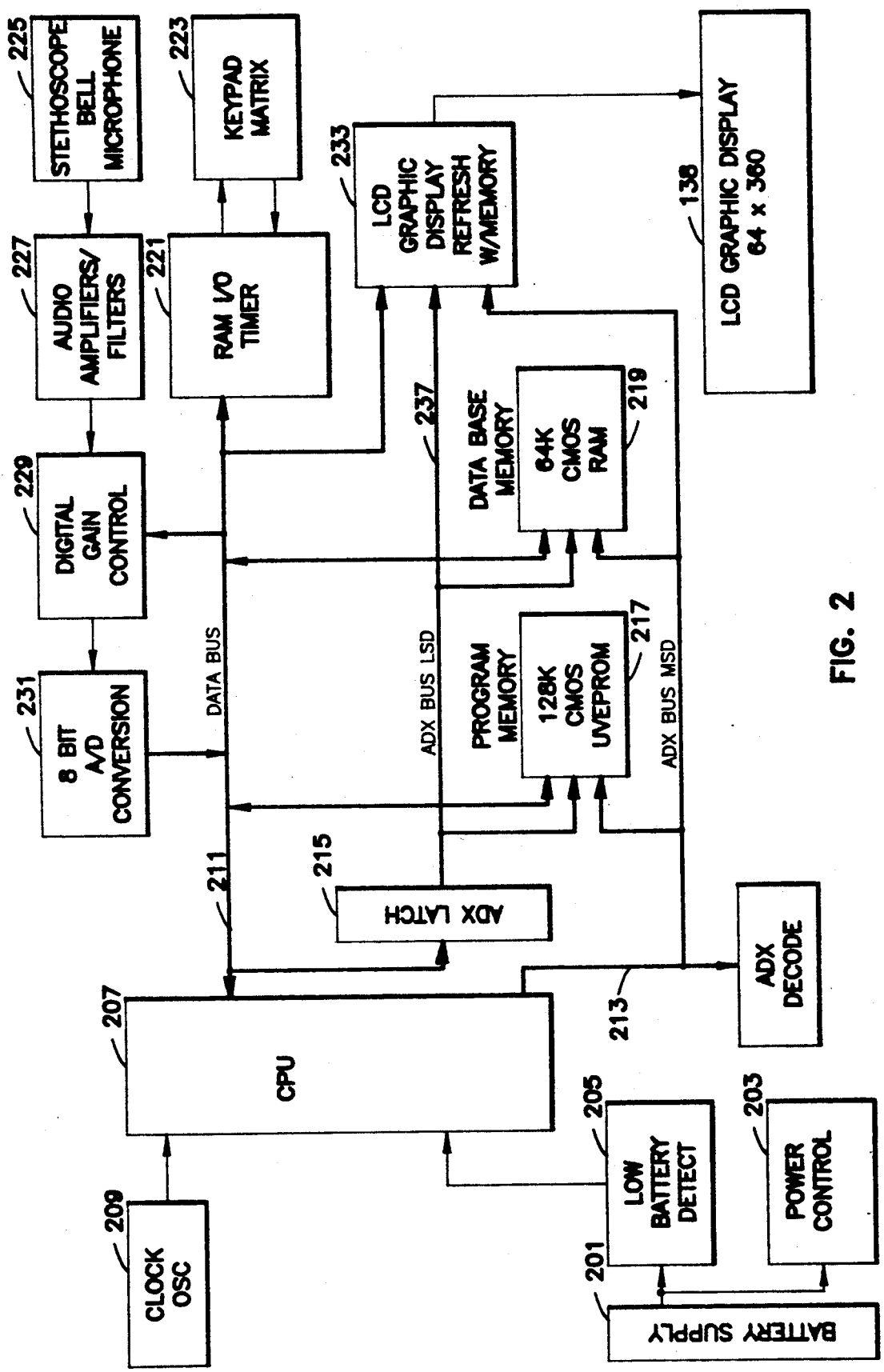
FIG. 2 is a block diagram of the microprocessor-based visual display stethoscope.

Referring to FIG. 2, a block diagram of the microprocessor-based architecture of the visual display stethoscope is shown. The battery supply 201 is used to power the electrical circuits of the visual display stethoscope, the power connections being omitted for clarity in the block diagram. The power control circuit 203 contains an auto shutdown circuit, a voltage regulator, and a voltage invertor section to generate a plurality of voltages from the single voltage derived from the battery supply 201. A low battery detect circuit 205 monitors the voltage level in the batteries and reports this condition to CPU 207.

An NSC800 microprocessor available from National Semiconductor forms the CPU 207 in the microprocessor-based architecture of the visual display stethoscope. Those skilled in the art will readily recognize that a wide variety of microprocessor types and microcontrollers can be used to implement the functions of the present invention. The preferred implementation uses an NSC800 microprocessor due to its availability and convenience in programming.

Clock oscillator 209 is used to generate the timing signals required by CPU 207 and to synchronize the functioning of the visual display stethoscope. Those skilled in the art will readily recognize the variety of implementations of oscillator circuit 209 and the need for such a circuit.

The architecture of the present design shown in FIG. 2 is bus-oriented with a multiplexed address-data bus 211 for the low-ordered 8 bits and a dedicated address bus 213 for the high-ordered 8 bits of the address. The address latch 215 is needed for proper decoding of the low-ordered address bits for addressing the memories 217 and 219.

The RAM and I/O timer circuit 221 is in the preferred embodiment a multi-function chip part number NSC810 also available from National Semiconductor and designed specifically to interface with the NSC800 microprocessor. This circuit 221 contains its own data and address decoding logic to effectively interface with data bus 211. The RAM and I/O timer circuit 221 monitors selected functions within the visual display stethoscope and interfaces to a keypad matrix 223 corresponding to the menu keys 140-148 found on display module 130. Keypad matrix 223 is used to enter command functions by the operator and to control the display.

Across the top of FIG. 2 is the input path for receiving the body sounds through the stethoscope bell microphone 225 found in the stethoscope bell 122. This microphone is attached to a high-gain audio amplifier and filter circuit 227 which in turn drives the digital gain control circuit 229. The gain of circuit 229 is digitally controlled off data bus 211 from CPU 207. The appropriate gain being programmed into gain control circuit 229 allows the correct amplification of the audio signals for appropriate analog to digital conversion by A/D converter 231. The results of the digitized audio signals is placed on data bus 211 for processing by CPU 207.

The software for operating the visual display stethoscope is contained in memory circuit 217. This software, described in detail below, controls the operation of the visual display stethoscope and performs the analysis of the body sounds received from the stethoscope bell 122 and displayed by the LCD graphic display 138. The display and analysis requires working memory located in database memory 219.

The LCD graphic display 138 in the preferred embodiment is a 64×400 pixel display capable of displaying analog representations of the body sounds and commands as to where to listen for the next body sound. The LCD graphic display 138 is microprocessor-driven through controller 233. The details of the hardware design are described below.

Figure 3A:
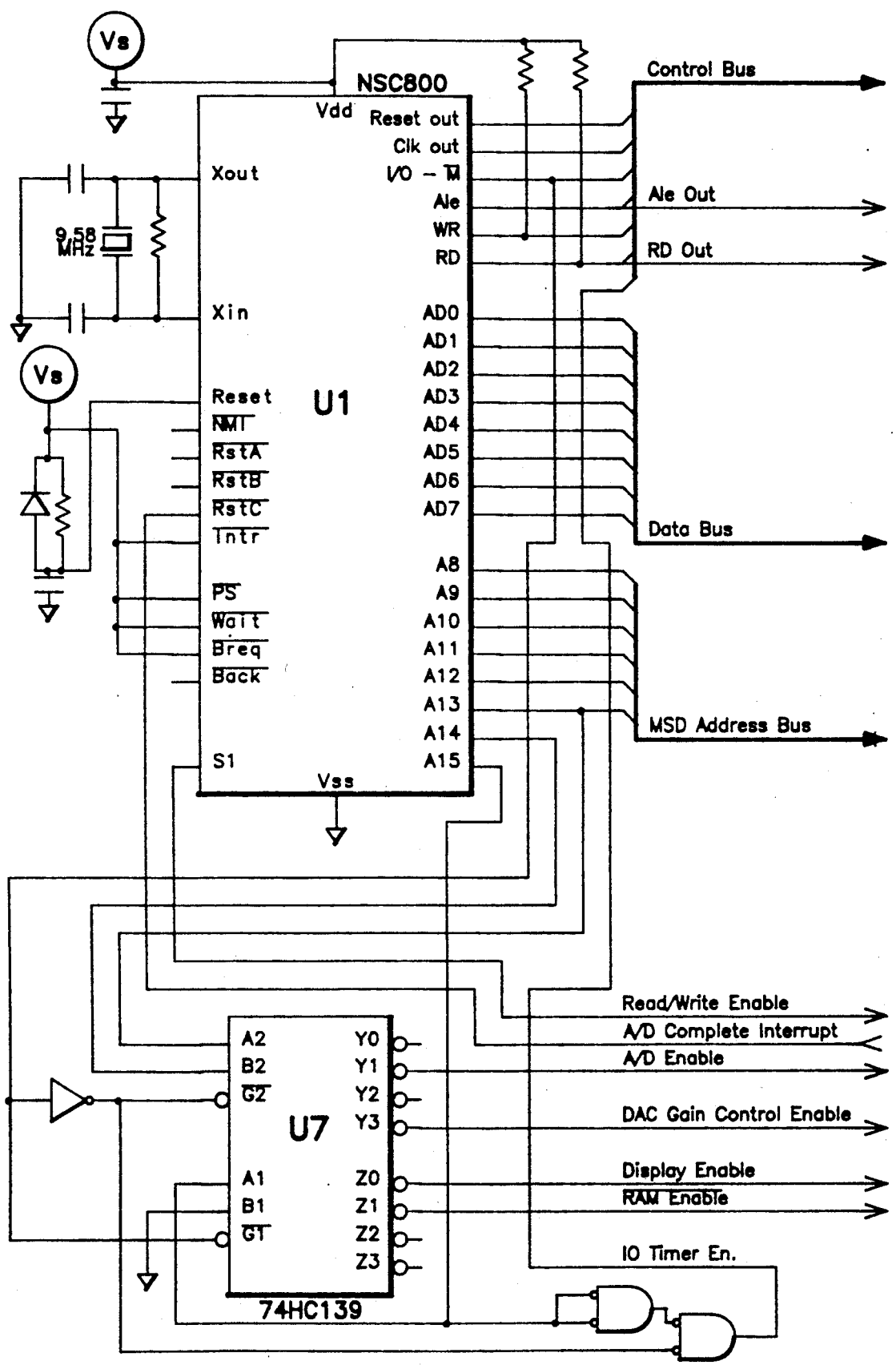

Referring now to FIGS. 3a-3i, the detailed electrical design of the visual display stethoscope will be described. The main power for the system is derived from a nominal 7.2 v NiCad rechargeable battery 302 as shown in FIG. 3i. The power control consists of three sections: an auto shutdown circuit, a 5 v $V_{cc}$ regulator, and a voltage invertor section to generate a $-7.5$ v $V_{ee}$.

The auto shutdown circuit of FIG. 3i is activated by closing the momentary "Power On" switch 150 found on the display module 130 of the visual display stethoscope.

Battery voltage $V_{bb}$ is switched to U16 and also the logic 1 voltage level at U16-1 sets the RS flip flop built from U16-2 and U16-3. The output of the RS flip-flop turns on NPN transistor Q1, the collector of which sinks current to the base of PNP transistor Q2. Q2 switches the battery voltage $V_{bb}$ to the flip flop and also the input of the monolithic voltage regulator U17 which, in the preferred embodiment is part number LM2931 available from National Semiconductor and other vendors. The output of regulator U17 supplies a current limited and thermal protected 5 vdc labeled $V_{cc}$. System common is labeled $V_{ss}$.

Upon Q2 switching on, the $V_{bb}$ (battery voltage) is also input to the voltage invertor circuit comprised primarily of integrated circuit U18. This circuit (part number MAX634 available from Maxim Semiconductor) creates a $-7.5$VDC from the positive battery voltage. The circuit also performs low battery detection from an internal voltage comparator and reference. The power to the system remains on until directed by the CPU to reset the RS flip flop and shut off Q2 which shuts off system power via the SYSTEM SHUTDOWN signal line.

Figure 3B:
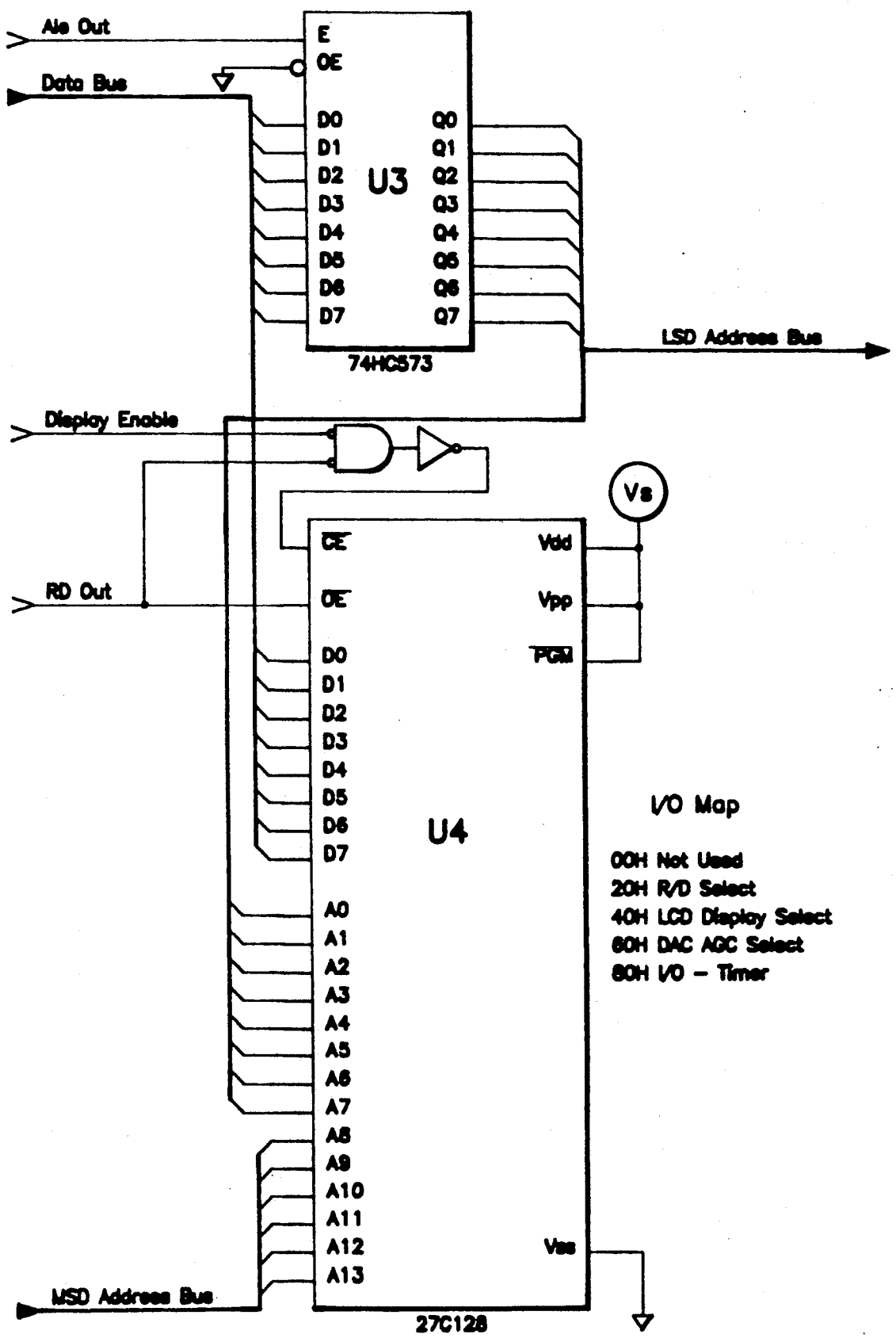

The control of the visual display stethoscope system is implemented by its Central Processing Unit (CPU) and memory shown in FIGS. 3a and 3b. The central processor U1 is an NSC800 which is an 8-bit CMOS bus-oriented processor. It implements a multiplexed address and data bus by which its peripherals exchange data. The memory is made up of 32K×8 of CMOS PROM and 32K×8 of CMOS RAM. The program memory U4 held in UV erasable PROM contains the system software. The RAM memory U5 is used for the storage and analysis of the digitized audio sounds. The address latch U3 latches the address from the CPU address/data bus during the first half of a memory access cycle.

The selection of peripherals which access the bus is done through an I/O—memory decoding process. The CPU can access 64K bytes of memory and 256 I/O addresses. The address decoding logic chip U7 (part number 74HC139 available from National Semiconductor and other vendors) generates select lines to each peripheral on the bus. The logic is divided into two sections; the memory and the I/O selects. The following is a memory and I/O map of the respective peripherals (shown in hexadecimal numbers):

| Ram Map | |
|---|---|
| 0000-7FFF$_H$ | PROM Memory |
| 8000-FFFF$_H$ | RAM Memory |
| I/O Map | |
| 20$_H$ | A/D Select |
| 40$_H$ | LCD Panel Interface Select |
| 60$_H$ | DAC AGC Select |
| 80$_H$ | I/O - Timer Select |

Figure 3C:
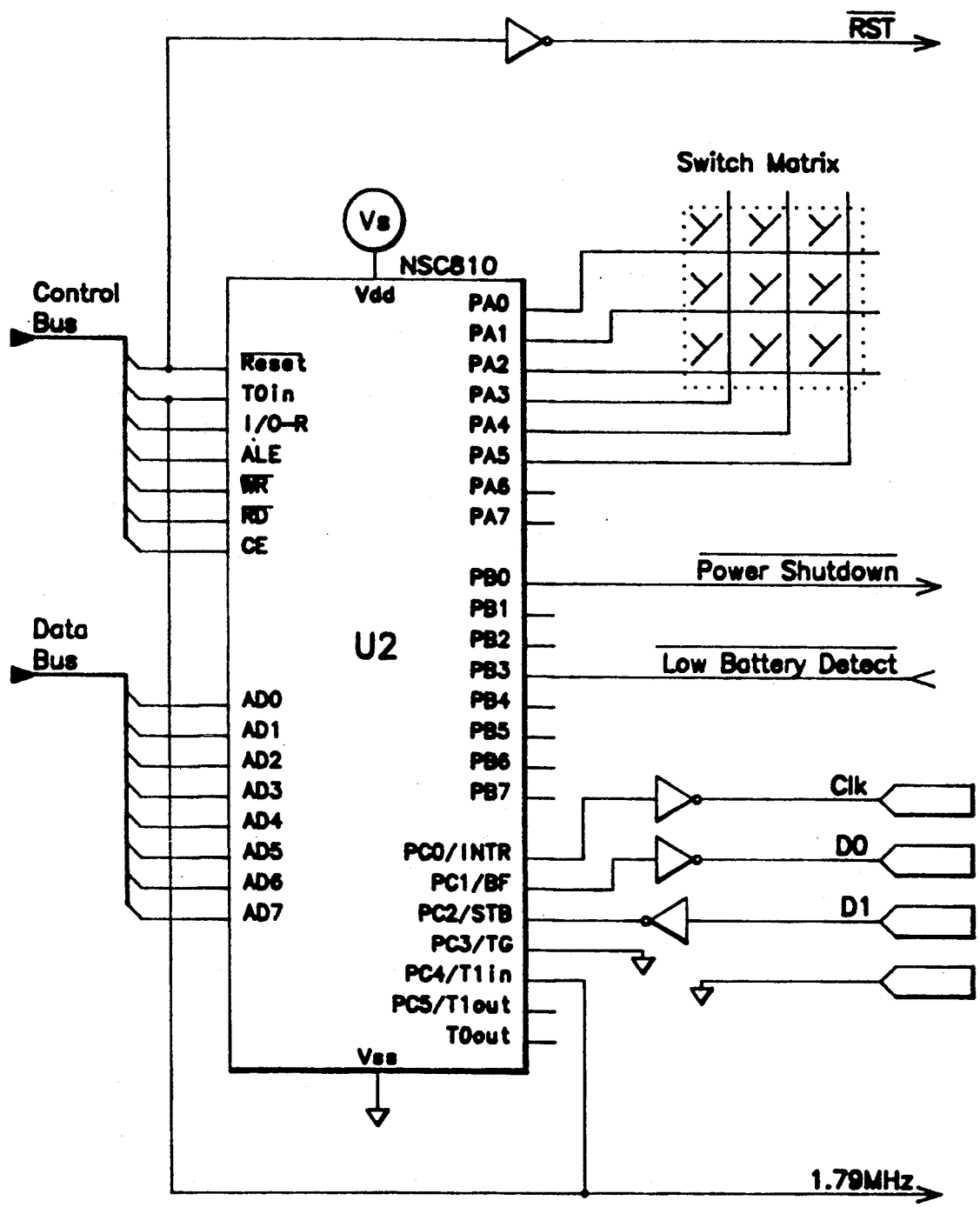

The CPU interface circuit U2 of FIG. 3c, attached to CPU U1 of FIG. 3a, is in the preferred embodiment part number NSC810 from National Semiconductor. This part is specially designed to operate with the NSC800 CPU to perform a plurality of timer, I/O and memory functions. There are 7 keys which operate the visual display stethoscope, six of which are "soft" keys configured in a 2×3 switch matrix driven by column and row I/O lines from the CPU interface circuit U2. One key (Power switch 150) is a control circuit and is used to activate initial power to the system. The other six keys in the matrix correspond to the menu keys 140-148 as shown in FIG. 1. The visual display stethoscope of the present invention is menu driven. Thus menu keys 140-148 are not dedicated to a particular function. Instead their function changes according to that shown on LCD graphic display 138. The various displays, menus, and functions are shown and described in detail below with respect to FIGS. 7a-7l.

Each of the menu keys 140-148 when pressed from MENU 1 or MENU 2 initiates one of the following functions of the visual display stethoscope:

| | Heart Mode Description |
|---|---|
| MENU 1 | |
| LOCATION | Selection of location on sternum diagram 132 with which electrical signals are associated in memory and during visual representation as waveforms of body sounds. |
| PAN | Manipulation of captured waveform to view additional segments of a captured waveform to left and right of the displayed segment of the waveform. |
| GAIN | Amplification of received body sounds by variable gain either according to user direction or automatically to achieve a full screen display. |
| RT FILTER | Real-time analog filtering of displayed body sounds to filter out low frequency components of the waveform for better visualization of certain high frequency abnormalities. |
| CLEAR | Deletion of electrical signals for each captured waveform stored in accordance with the location indicated the sternum diagram. |
| GO TO MENU 2 | Results in display of MENU 2. |
| MENU 2 | |
| LOCATION | Selection of location on sternum diagram 132 with which electrical signals are associated in memory and during visual representation as waveforms of body sounds. |
| SCALE | Manipulation of a user selected portion of captured waveform to alter visual representation, e.g., to expand to X2 or X4 horizontal display or to compress to X2, X1 horizontal display. |
| TIME | Allows for precise time interval measurements wherein a user sets the time interval to be measured and the measurement is displayed on LCD graphic display. |
| PC FILTER | Post capture high pass digital filtering of captured and saved body sound waveforms for post examination study. |
| SET-UP | Allows a user to set up various programmable options, such as self-testing, battery detect, language, operation of the sweep key, etc. |
| GO TO MENU 1 | Results in display of MENU 1. |

Sub-menu functions are further shown in FIG. 7a-7l and described in the corresponding portion of this Detailed Description.

The detailed electrical connections between the components shown in FIGS. 3a and 3b provide a microprocessor base on which the software will operate. The microprocessor, memory components and peripheral drivers and receivers operate both to control the functions of the visual display stethoscope and to perform signal processing on the body sounds. Those skilled in the art will readily recognize many equivalents to the detailed electrical configurations shown in FIGS. 3a and 3b which illustrate only a preferred embodiment for the present invention.

Figure 3D:
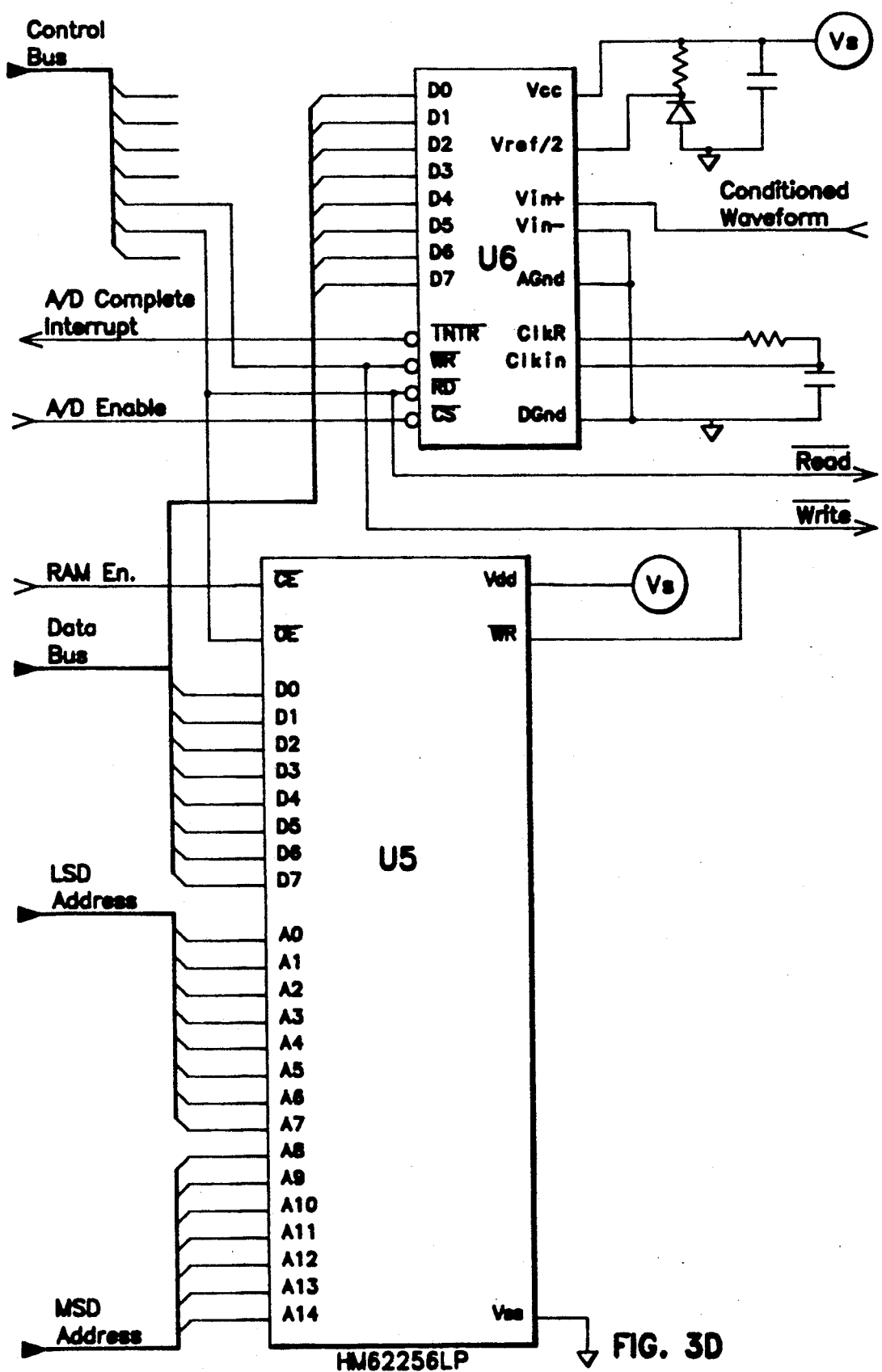
Figure 3E:
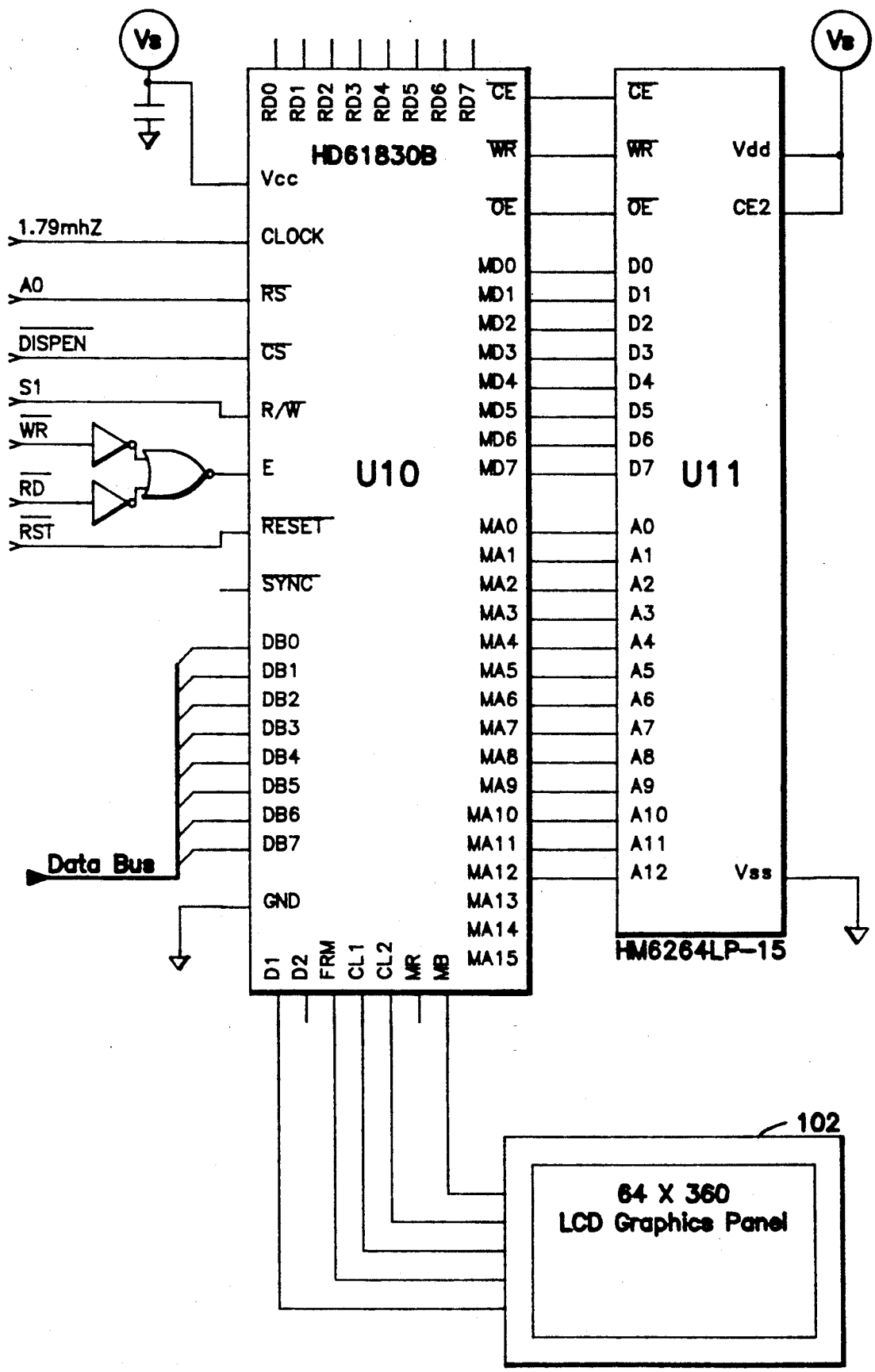
Figure 3F:
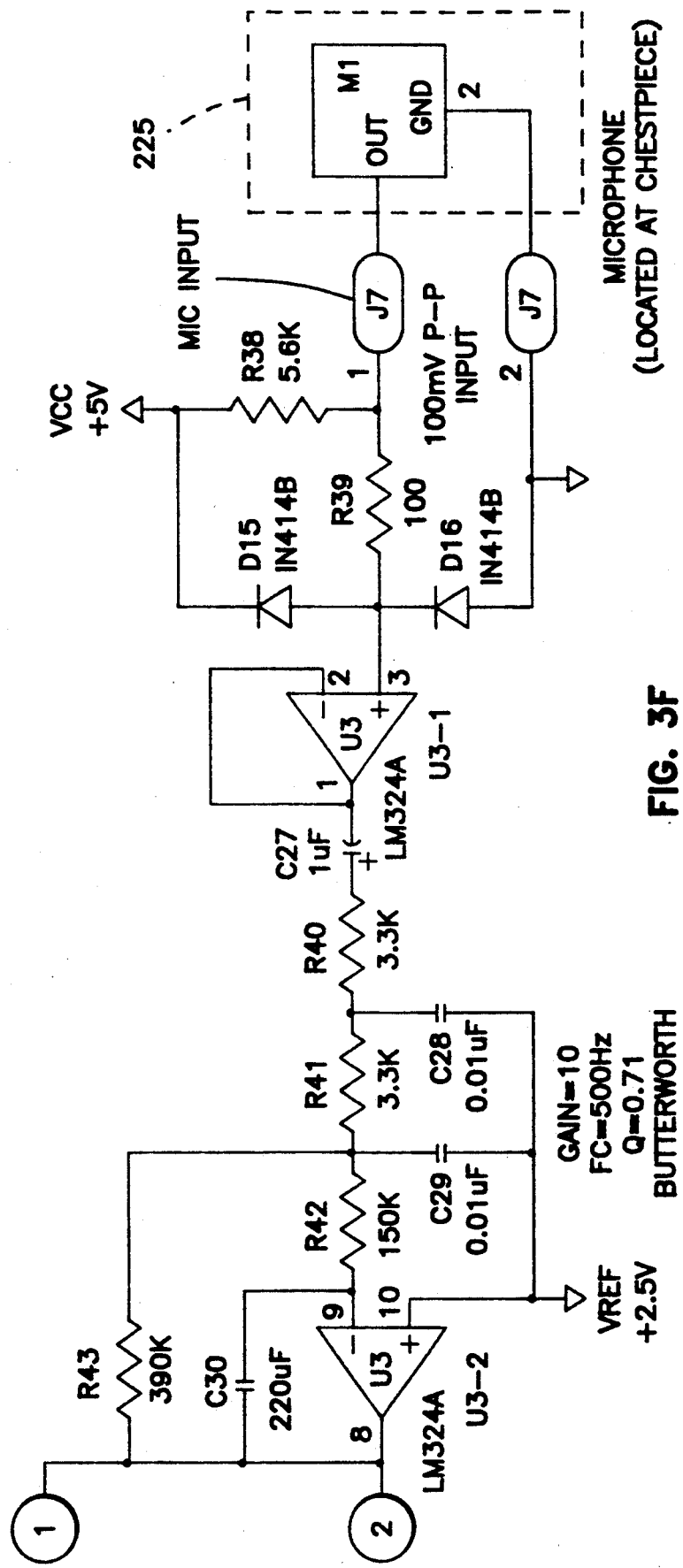
Figure 3G:
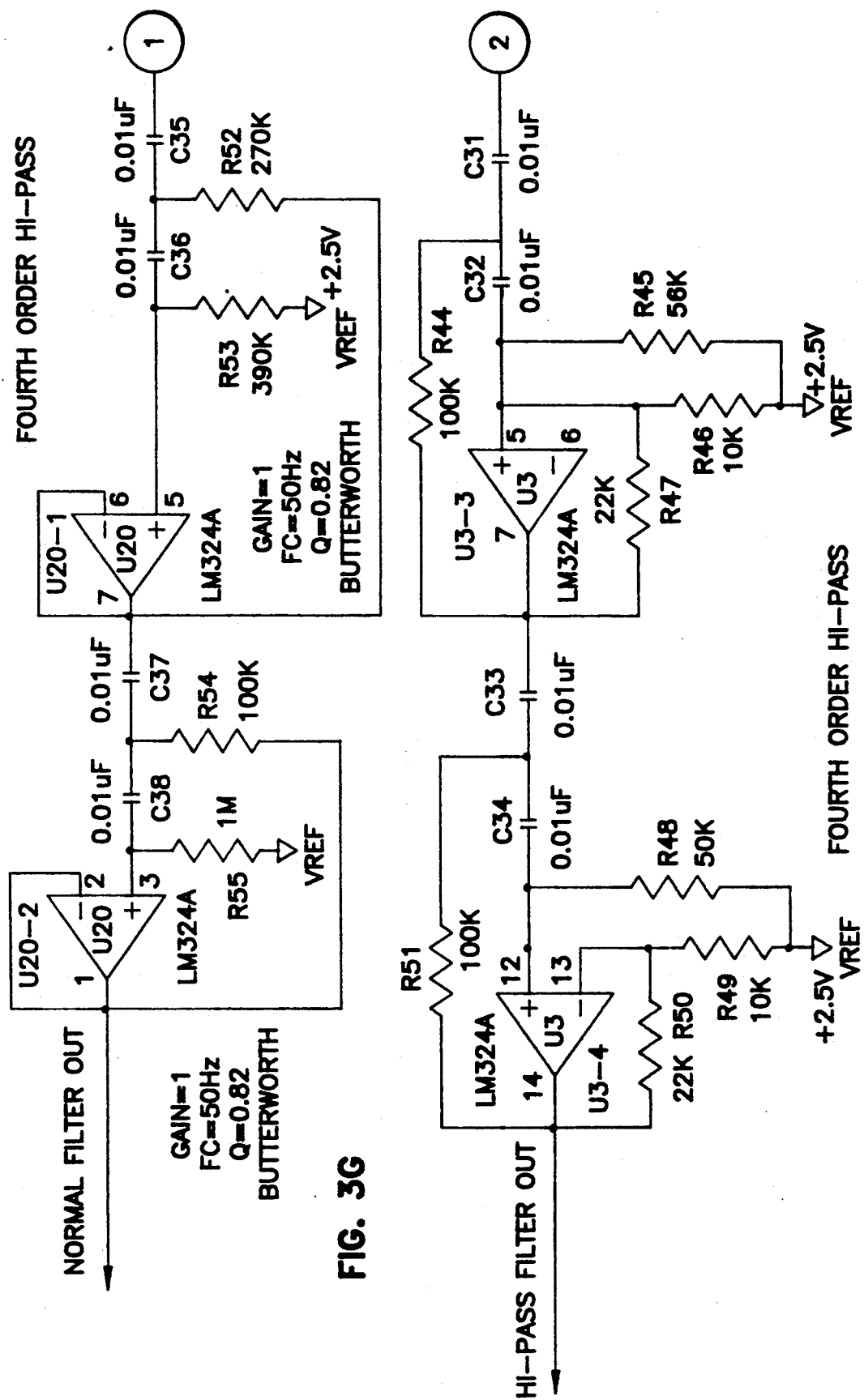

Referring to FIGS. 3f and 3g, the miniature microphone 225 is mounted in stethoscope bell 122 of the visual display stethoscope where the sound pressure from the body is picked up. The actual sound waves picked up by the bell are passed intact to the stethoscope's earpieces so that the user may hear the acoustic information just as it is received by the microphone of the visual display stethoscope. The microphone used is not of a critical type and is of a common variety. The sensitivity of the microphone should go down to at least −65 dB referenced to 0 dB=1 v/μbar at 1 kHz. The output of the microphone is amplified and forwarded to the PCB assembly via a ground shielded cable. The audio heart sounds are converted by the microphone to electronic heart sounds and are DC biased to half the supply.

The electronic heart sounds are first buffered by unity-gain amplifier U3-1 and then are passed through a low pass active filter utilizing operational amplifier U3-2, which will attenuate frequency components greater than 500 hz at a rolloff rate of 12 dB/octave and also amplify the filtered signal by a gain of 10. The filter functions as an antialiasing filter for the sampled data system which samples at a 2KHz rate.

The signal is then passed through two stages of high pass filter utilizing operational amplifiers U3-3 and U3-4 which will attenuate frequencies below 50 Hz at a rolloff rate of 24 dB/octave. The signal is also passed through two parallel stages of hi-pass filter utilizing operational amplifiers U20-1 and U20-2 which will attenuate frequencies below 200 hz at a rolloff rate of 24 dB/octave. All the filters are designed to have a maximally flat response with a $Q=0.5$. The visual display stethoscope of the present invention enables the user to select which analog filter path signal (NORMAL or HI-PASS) is displayed on LCD graphic display 138 as shown in FIG. 1. This is done in the RT FILTER or PC FILTER Function described above and also further described below. Those skilled in the art will readily recognize that any of a number of switching mechanisms widely and commonly known in the art could be used to accomplish this function. The HI-PASS filtered signal may be helpful in allowing better visualization of high frequency heart murmurs such as aortic insufficiency by filtering out the low frequency components of the body sound signal.

Figure 3H:
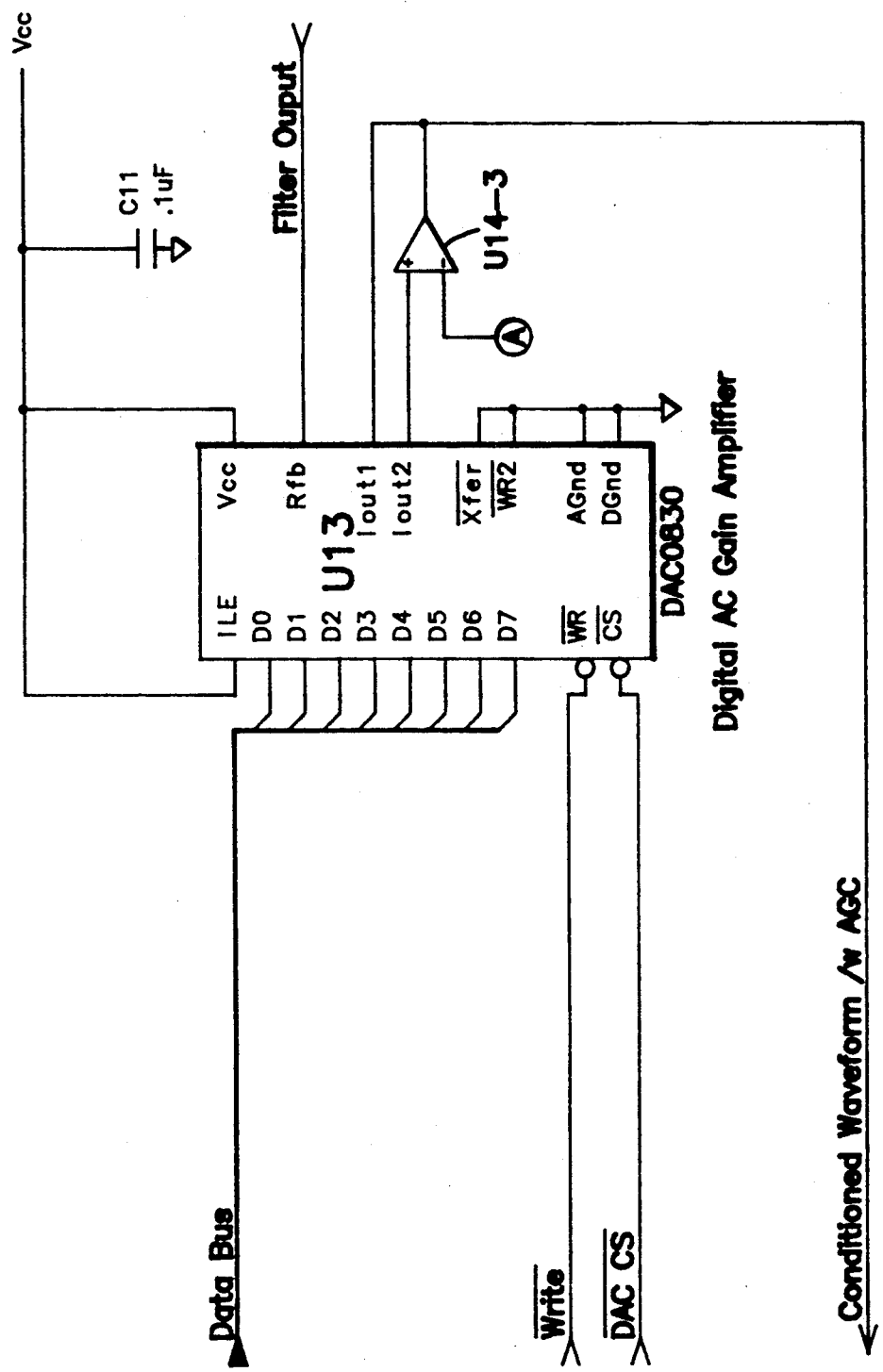
Figure 31:
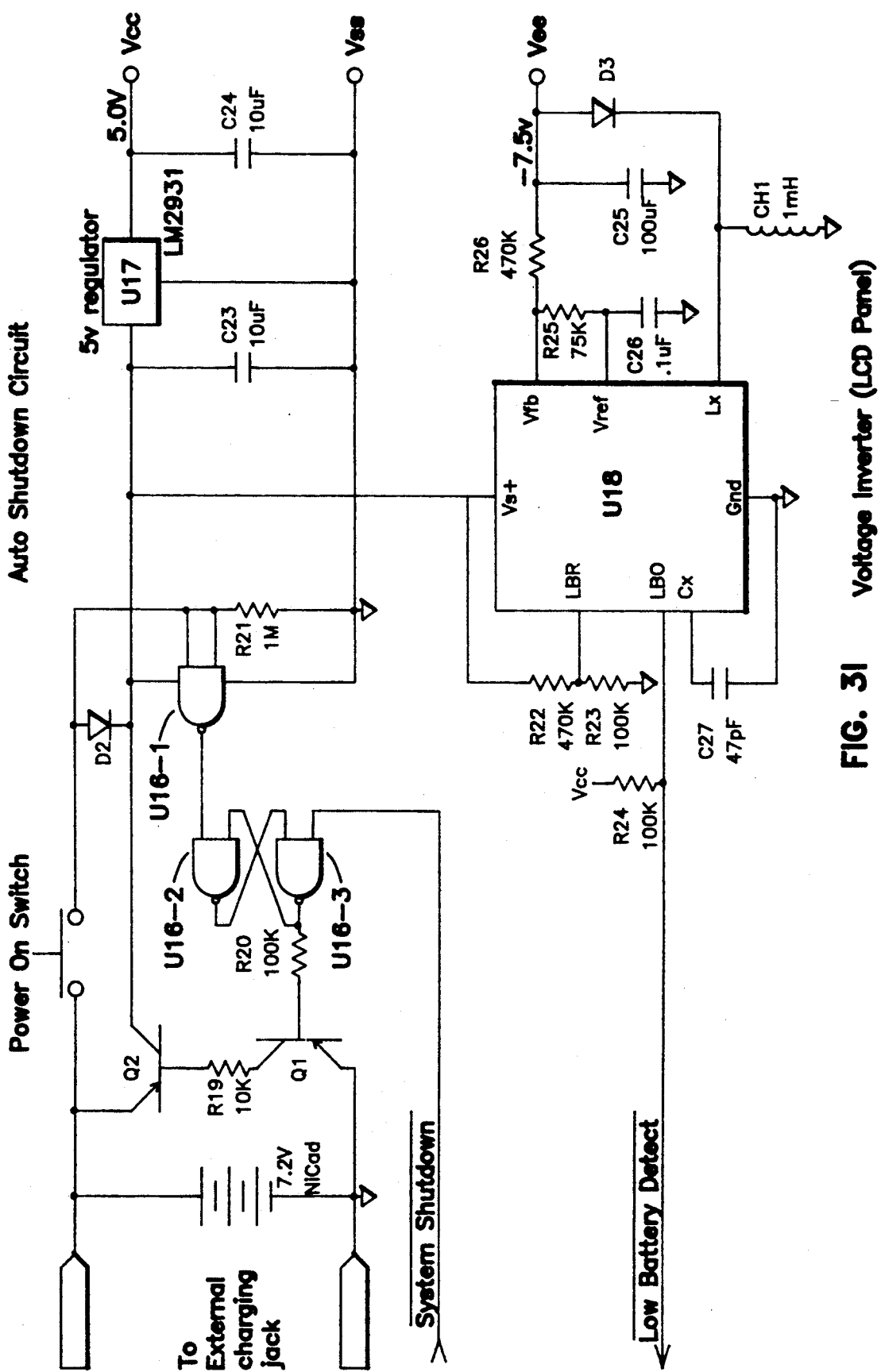

The need for the gain control circuit comprised substantially of U13 and U14-3 shown in FIG. 3h is because the amplitude of heart sounds from various patients will vary. In order to perform valid waveform analysis, the amplitudes are scaled to nominal values. The digital gain control circuit will, under CPU control, automatically adjust the gain of the incoming cardiac sounds to conform to a preset nominal level. The digital gain is performed by implementing a digital to analog converter (DAC) U13 (part number DAC0830 available from National Semiconductor and other vendors) in the feedback loop of operational amplifier U14-3. Gains of 1–256 can be realized by writing to the 8 bit input register of the DAC U13. The output of the digital automatic gain control circuit will always be adjusted so that peak heart sound waveforms are at a nominal level.

The analog to digital conversion (A/D) is a process by which the conditioned heart sounds are digitized and stored in data base memory. Referring to FIG. 3d, circuit U6 is controlled by the CPU and performs the A/D function. This circuit is in the preferred embodiment part number ADC0801 available from National Semiconductor and other vendors. The audio waveform from the signal conditioning circuitry of FIG. 3d is sampled at a 2KHz rate (every 500μs). The analog value is converted into an 8-bit digital equivalent and stored in RAM memory U5. In order to digitize a full cardiac cycle (max of 1.2 sec), 2,400 samples are taken and stored at data base RAM memory U5 for future analysis.

The A/D converter U6 accepts inputs from between 0–5V. In the preferred embodiment, a 2.5V baseline is used and the A/D converter accepts ±2.5V signals. A precision voltage reference U12 (part number LM336 from National Semiconductor) is used to reference the incoming analog signal to a full scale input. The CPU U1 writes to the A/D converter U6 to initiate the conversion process. When the conversion is complete, U6 interrupts the CPU U1 and the data is read from the data bus and written into memory U5.

The LCD panel interface U10 shown in FIG. 3e is an intelligent controller which coordinates the functions and generate the signals necessary to drive an LCD graphic display 138. The interface circuit U10 is connected to the CPU data bus and control signals and is in the preferred embodiment part number HD61830B available from Hitachi Semiconductor. In conjunction with the interface is a CMOS memory circuit U11 which contains the data which is currently being displayed on the LCD graphic display 138. The LCD panel 102 is autonomously refreshed from the signals generated by the interface circuit and the data patterns stored in RAM memory U11. The display changes by the CPU directing a set of commands to the interface circuit and modifying the display RAM memory, and in turn the display.

The LCD graphic display 138 is available from Optrex Corp. and is made up of dots or pixels. The matrix is configured as 64 vertical×400 horizontal dot resolution. The panel will display graphic cardiac waveforms along with alphanumeric characters during the procedures for waveform capture, display, and manipulation.

The visual display stethoscope system also has a three wire interface for asynchronous serial communication to dedicated peripherals (not shown). These peripherals would be used for plotting waveforms, or storage of the waveform data base memory for future retrieval. The I/O interface circuit U2 of FIG. 3c uses its programmable I/O lines to generate one output line and one input line for the peripheral interface.

Software Description

The software, programmed to run on the CPU 207 and held in memory 217, shown in FIG. 2 drives the hardware and directs the operation and control of the visual display stethoscope. This software is detailed and described in the flow diagram in FIGS. 4a–4c. Reference to the hardware schematics (FIGS. 3a–3i) should also be made while reading the following description of the operational flow.

Operational Flow

Figure 4A:
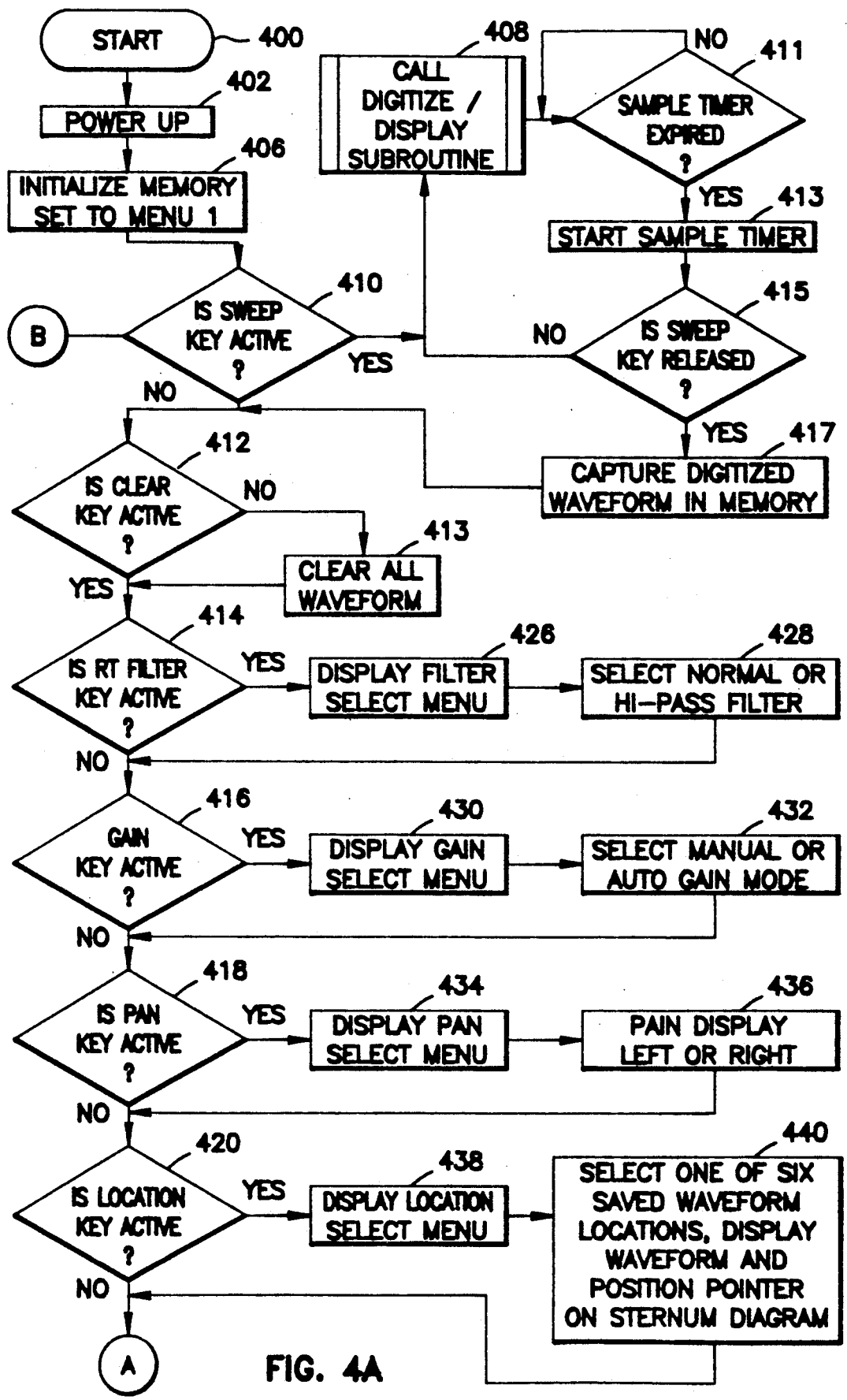
Figure 4B:
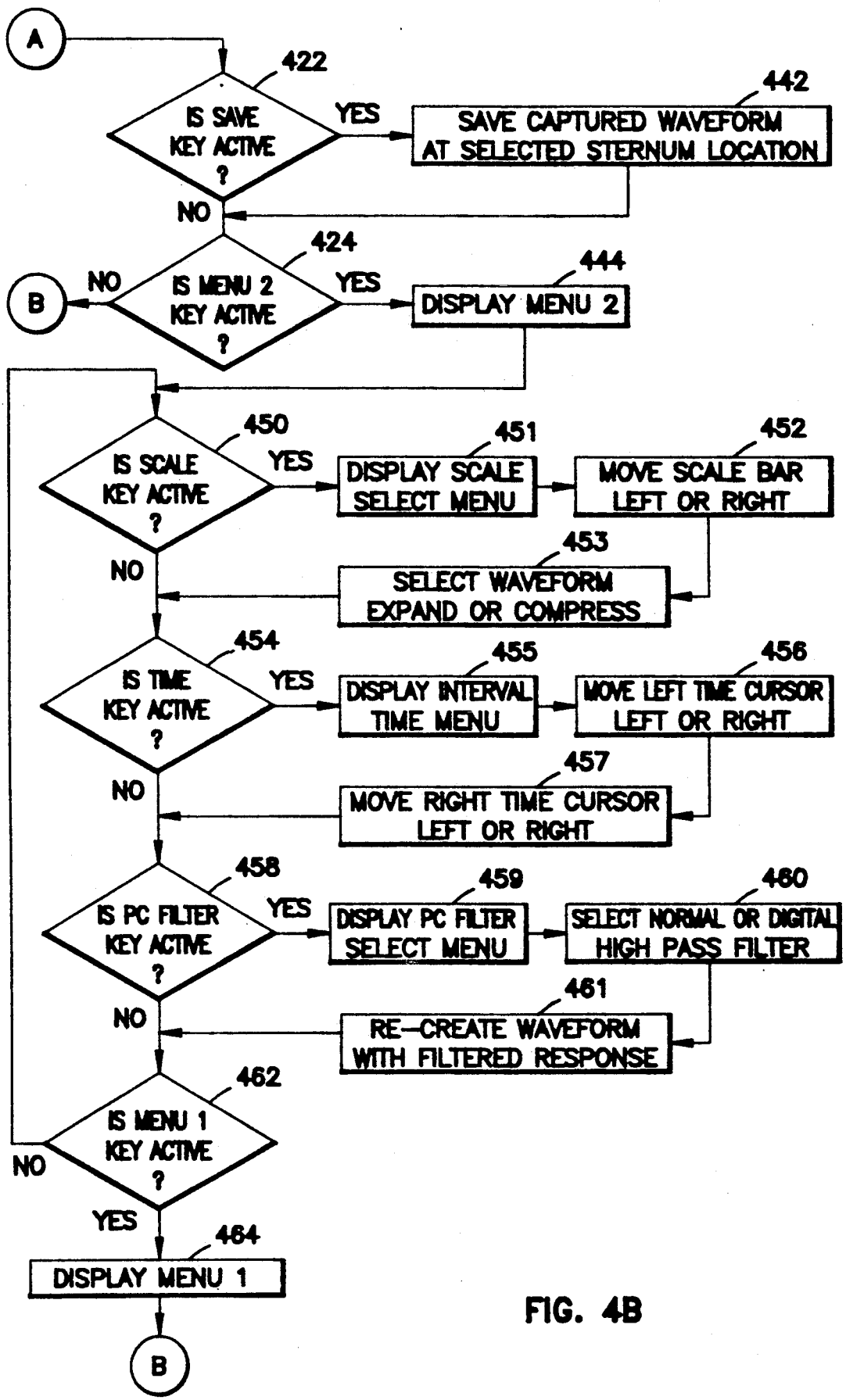
Figure 4C:
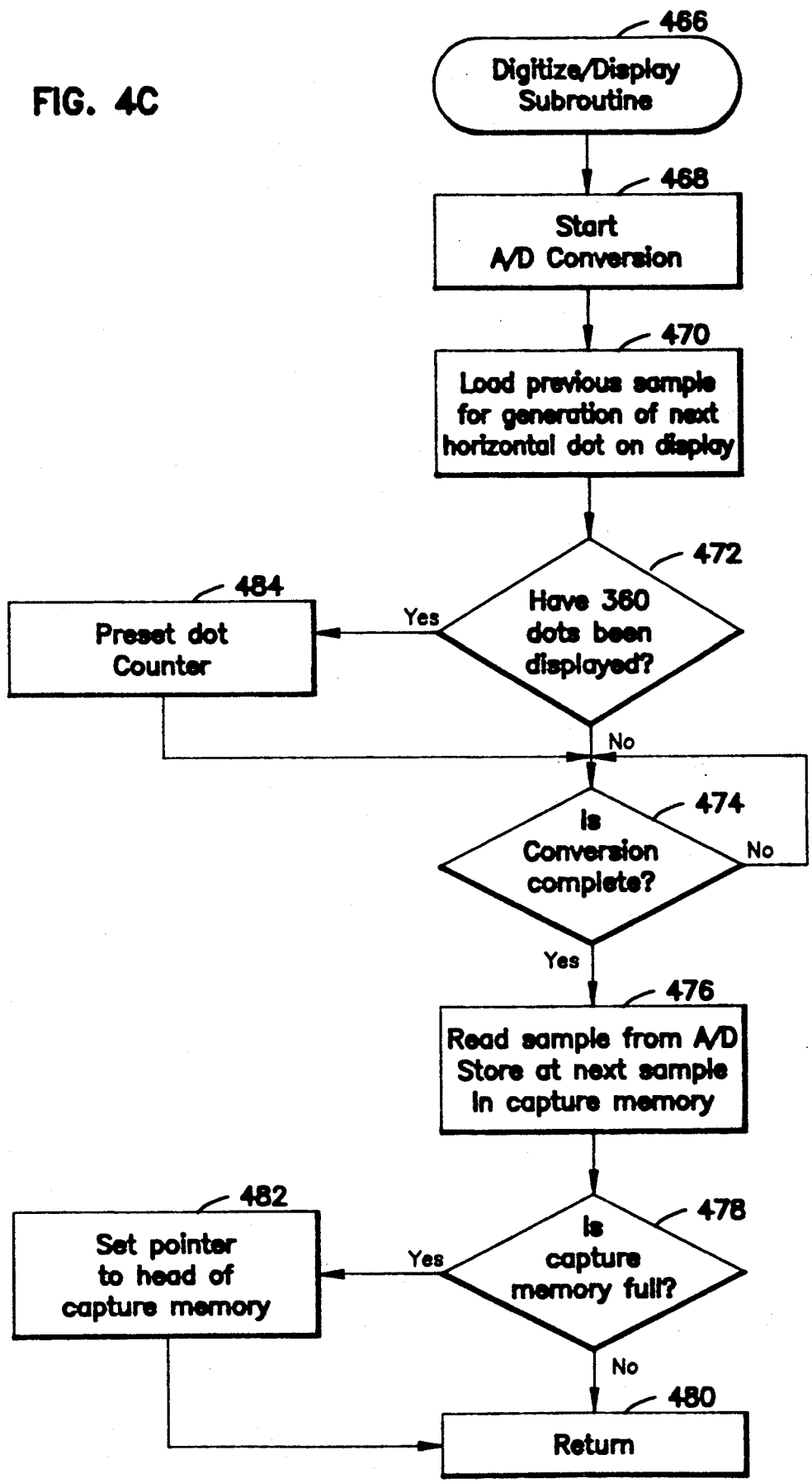

The operational flow and housekeeping duties performed by the microprocessor in the preferred embodiment of the present invention are described in FIGS. 4a–4c. Reference to electrical schematic diagrams 3a–3i will be helpful for a full understanding of the present invention.

The main control flow begins in FIG. 4a in box 400. The system is powered up at box 402 by a momentary closure of the power switch. The mode of operation is initialized at MENU 1, with a default sternum display 132 to 2RICS for a second right intracostal auscultation. (This default screen is shown on LCD graphic display 138 of FIG. 1.) If the memory was not cleared from the previous use, LCD graphic display 138 shows the last waveform present on the display prior to power down.

Next, the various MENU 1 keys 140-148 are polled to determined the next function to be performed. For example, at decision box 408 the sweep switch is polled. If the sweep switch is pressed the Digitize/Display subroutine 410 (shown in FIG. 4c) is called. Upon exit of the digitized display subroutine, a loop is repeated out of decision box 411 until a sample timer has expired, at which point the program control flow to enter box 413 were a sample timer is restarted and the next sample is taken. If at decision box 415 the sweep switch is not released, the next sample is taken. However, if at decision box 415 the sweep switch is released, the program control flow enters box 417 where the digitized waveform is captured and saved into memory.

The MENU 1 keys continue to be polled by the microprocessor to test for additional control operations. In order to poll the keys on the keyboard, decision boxes 410-424 comprise a polling control flow to check the status of the keys. The sweep switch is polled by decision box 410, the CLEAR key is polled by decision box 412, the RT FILTER key is polled by decision box 414, the GAIN key is polled by decision box 416, the PAN key is polled by decision box 418, the LOCATION key is polled by decision box 420, the save key is pulled by decision box 422, and the GO TO MENU key is polled by decision box 424. The control loop is continued from decision box 424 through the continuation bubble B in FIG. 4b back to decision box 410 in FIG. 4a, forming a loop to continually poll the keyboard and determine whether any of the menu keys 140-148 have been pressed.

If menu key 147 associated with the CLEAR function has been pressed, control is passed from decision box 412 to box 413 where all electrical signals comprising captured waveforms and data are cleared from memory.

If menu key 146 associated with the RT FILTER function has been pressed at decision box 414, control is passed to box 426 where the filter select menu is displayed. The user selects NORMAL or HI-PASS filter at box 428.

The software flowchart for implementing the real time filter select is shown in FIG. 4d. The NORMAL and HI-PASS filter keys are polled to determine which filter path (the circuits for which are shown in FIG. 3f and 3g) is selected. If the NORMAL filter key is selected at decision box 802, the NORMAL filter path having a bandwidth of 50-500 hz is selected at box 804. If the HI-PASS filter key is selected at decision box 806, the HI-PASS filter path having a bandwidth of 200-500 hz is selected at box 808. The selection is accomplished via a select line on CPU interface circuit U2 (as shown in FIG. 3c). If the EXIT key is selected at decision box 810, a new one is displayed at box 812.

Referring again to FIG. 4a, if menu key 144 associated with the GAIN function is depressed at decision box 416, the GAIN select menu is displayed at box 430. The user then selects MANUAL or AUTO gain mode at box 432.

If menu key 142 associated with the PAN function is depressed at decision box 418, the PAN select menu is displayed at box 434, and the user is able to pan the display left or right at box 436.

If menu key 140 associated with the LOCATION function is depressed at decision box 420, the LOCATION select menu is displayed at box 438. From this menu, one of six saved waveform locations is selected and the corresponding waveform and position pointer on sternum diagram 132 is displayed at box 440.

If the save key 136 is depressed at decision box 422, the captured waveform is saved in memory 219 shown in FIG. 2.

If menu key 148 associated with the GO TO MENU 2 function is pressed at decision box 424, MENU 2 is displayed at box 444. If the MENU 2 key is not depressed, the MENU 1 keys continue to be polled by the microprocessor to test for additional control operations.

Once MENU 2 is displayed, the MENU 2 keys are polled in a similar manner as described above with respect to the MENU 1 keys. For example, if the menu key associated with the SCALE function is depressed at decision box 450, the SCALE select menu will be displayed at box 451. At that point, the user can move the scale bar on the LCD graphic display 138 left or right at box 452 and can select waveform expand or compress at box 453.

If the menu key associated with the TIME function is depressed at decision box 454, the TIME menu is display at box 455. The user may then move the left and right time cursors to the desired position on the displayed waveform to set the time interval to be measured. The measurement taken is displayed on LCD graphic display 138. This function allows a user to perform specific interval timing on strategic valvular events for the study and recognition of abnormalities.

A more detailed software flowchart for implementing the TIME function is shown in FIG. 4e. Once the interval time menu is selected and displayed, at box 455 of FIG. 4b, the left and right cursor keys are polled in a loop comprised of decision boxes 814-822. If the left cursor left key is pressed at decision box 814, the left cursor is moved left one pixel position on LCD graphic display 138 at box 824. If the left cursor right key is pressed at decision box 816, the left cursor is moved right one pixel position on LCD graphic display 138 at box 826. If the right cursor left key is pressed at decision box 820, the right cursor is moved left one pixel position on LCD graphic display 138 at box 828. If the right cursor right key is pressed at decision box 822, the right cursor is moved right one pixel position on LCD graphic display 138 at box 830. The time interval between cursors is calculated at control box 832, and is displayed on LCD graphic display 138 at control box 834. The calculation is based on the amount of time between each pixel held in memory. The number of pixels is multiplied (summed) by the time interval between each pixel to give the measurement between the cursors.

Although the preferred embodiment of the present invention uses cursors as the means by which a user can indicate a desired time interval to be measured, those skilled in the art will readily recognize and appreciate that any of a number of indication schemes could be substituted therefor without departing from the spirit and scope of the present invention. For example, the visual display stethoscope of the present invention could be configured to allow the user to enter such information through a numerical keypad, a light pen, a touch screen, etc.

Referring again to FIG. 4b, if the menu key associated with the PC FILTER function is depressed at decision box 458, the PC FILTER select menu is displayed at box 459. This function is used for post capture digital filtering of saved waveforms. The user can then select NORMAL or digital HI-PASS filter at box 460 and the waveform with filtered response is recreated at box 461. The HI-PASS filter function filters out low frequency components of the displayed waveform thus giving the user a better display of the high frequency components for easier recognition of high frequency abnormalities such as aortic insufficiency.

A more detailed software flowchart for implementing the PC FILTER function is shown in FIG. 4f. Once the postcapture filter menu is displayed at box 459, the HI-PASS filter and NORMAL filter keys are polled in a control loop shown in FIG. 4f comprised of decision boxes 840, 842, and 844. If the HI-PASS filter key is pressed at decision box 840, an FIR digital filter transformation algorithm is performed on the captured waveform in memory 219. The resultant HI-PASS filtered waveform is output to the LCD graphic display 138 at control box 848. If the normal filter key is pressed at decision box 842, the original filtered waveform is output to the LCD graphic display 138 at control box 850. If the EXIT key is depressed at decision box 844, MENU 2 will be displayed at box 852.

Referring again to FIG. 4b, if the MENU 1 key is active at decision box 462, MENU 1 will be displayed at box 464. If the MENU 1 key is not active, the MENU 2 poll loop will continue to poll the MENU 2 keys for additional control operations.

Referring once again to FIG. 4a, the Digitize/Display subroutine called from control box 408 performs the function of capturing the heart sounds, digitally encoding and storing them in memory and displaying the analog representation on the display. The flowchart for this subroutine is described in shown FIG. 4c. Control enters Digitize/Display subroutine at location 466. Command box 468 commences the analog-to-digital conversion process under microprocessor control and timing. As each digital sample from the A-to-D converter is received, it is used by the display driver to generate the dots on the display as shown in command box 470. Decision box 472 determines whether 360 dots along the horizonal axis have been displayed on the LCD display. If 360 dots have been displayed, the dot counter is preset by command box 484 and control is passed to decision box 474. At this location, a tight loop is performed until the A-to-D conversion is complete. This tight loop is necessary since the display of the previously loaded data can often be completed before the A-to-D conversion for the particular sample may be completed. Thus, decision box 474 and its associated tight loop ensures that subsequent processing is delayed until the completion of both A-to-D conversion and display functions.

Once the A-to-D conversion process is complete, control is passed to command box 476 where the just-completed sample is loaded into the capture memory for display while the next sample is converted by the A-to-D converter. Control is then passed to decision box 478 where the capture memory is checked to determine if is full. If so, control is passed to command box 482 where the pointer into the capture memory is reset to the head. Regardless of the status of the capture memory, however, control is passed back through return box 480 to the main calling routine in shown in FIG. 4a.

LCD Graphic Display

The LCD graphic display 138 as shown in FIG. 1 will now be explained.

Display 138 is in the preferred embodiment an LCD graphic display which is adapted for displaying the visual representation of received body sounds on a 2-dimensional x-y axis, wherein time is represented on the x-axis and amplitude is represented on the y-axis. Those skilled in the art will readily appreciate, however, that other variables could be represented on LCD graphic display 138 without departing from the scope of the present invention. For example, a frequency domain representation of the received body sounds would be displayed, or other variables such as pressure could also be displayed. In the preferred embodiment of the present invention, at the far left of LCD graphic display 138 is sternum diagram 132. Sternum diagram 132 has pointers for indicating where from what point on the body waveform data is to be taken and/or stored, or for indicating from what point of the body a body sound previously saved was taken. By pressing the appropriate key, a user can select the desired location on the sternum diagram.

Figure 5:
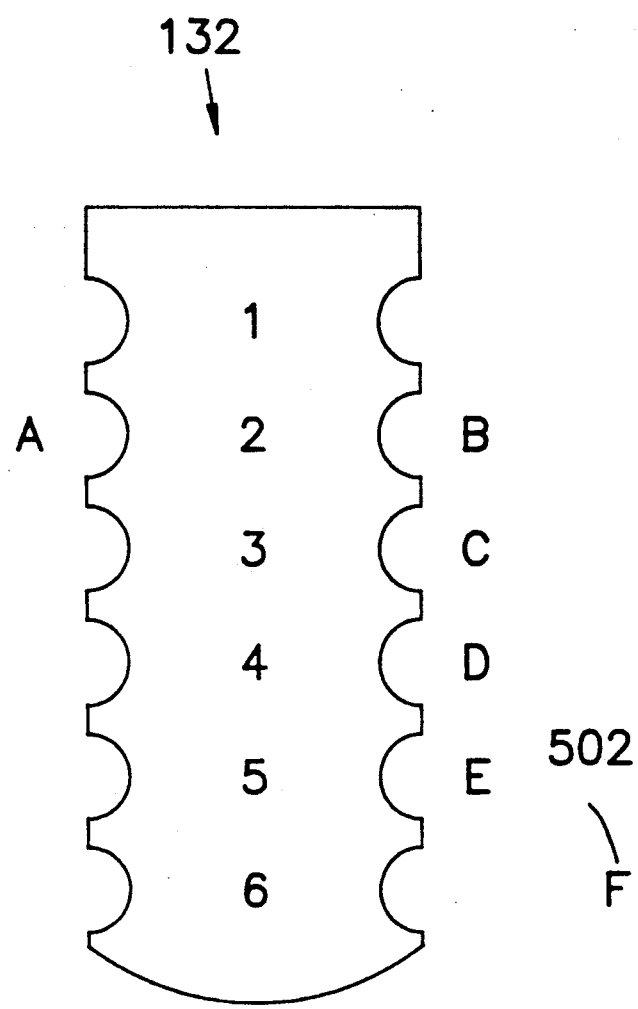
FIG. 5 is a closeup view of a portion of the display of the visual display stethoscope which depicts the seven chest wall locations to be recorded.

The preferred embodiment of the present invention is especially adapted for the auscultation of heart sounds. For this purpose, the stethoscope bell is applied to the chest wall in six specific locations. The preferred embodiment of the present invention includes a sternum diagram 132 on LCD graphic display 138 which contains pointers to these six locations. These locations are detailed in FIG. 5:

| | | |
|---|---|---|
| 1) | Right second intercostal space | (A) |
| 2) | Left second intercostal space | (B) |
| 3) | Left third intercostal space | (C) |
| 4) | Left fourth intercostal space | (D) |
| 5) | Left fifth intercostal space | (E) |
| 6) | The apex | (F) |

The sixth position at the apex will be located by listening for the point of maximum intensity (PMI) through the area of the apex, i.e. from the lower left sternal border to the left anterior axillary line, and by visual determination of the waveform of greatest magnitude on the display as the bell is moved through the area of the apex. A specific order of auscultation will be followed when obtaining the six locations by observing the location of a marker on the LCD sternum diagram 132 which will constantly illustrate the location to obtain next.

Confirmation that a good signal is obtained in each of the six locations will be obtained by viewing the waveform on the display while simultaneously listening to the audible signal through the earpieces. When the user has confirmed a good signal is obtained sweep switch 134 is released, which will freeze the waveform on the display. The user can then visually inspect the waveform before sending it to memory by pressing save switch 136. If a poor quality waveform is recorded inadvertently, the user can record a substitute waveform by moving a cursor to the desired location on sternum diagram 132 and repeating the recording for that location.

Although the preferred embodiment is especially designed for use in the auscultation of heart sounds, the present invention is applicable to more than simply diagnosing cardiac abnormalities via auscultation. Those skilled in the art will readily recognize that the present invention is also applicable to the analysis of bruits, lung abnormalities, or any other abnormality which can be studied and analyzed via auscultation methods.

Figure 6:
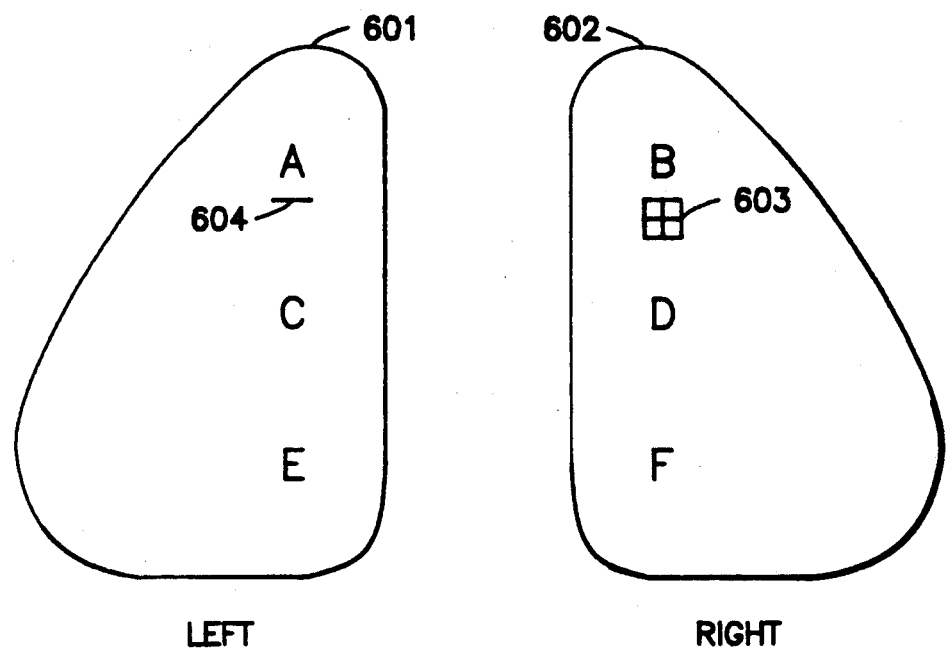
FIG. 6 shows an alternate display for the visual display stethoscope which directs the specific locations to be monitored for lung sounds for the application of the visual display stethoscope to lung sounds.

For example, in an alternate preferred embodiment of the present invention, the sternum display 601 is replaced by the lung display 601 and 602 shown in FIG. 6 and used on the LCD graphic display 138 for indicating the locations from which a physician should use the visual display stethoscope to take breath sounds. The lung display is similar to the cardiac sternum display described above in that the user is prompted as to where to place the bell of the visual display stethoscope to receive auscultation information. For example, in a fashion similar to that used in the sternum display, six locations over the lungs entitled A-F are used to prompt the user as to where to listen and store breath wave forms. The A means that a waveform taken at location A has been captured and stored in memory. The box display 603 indicates the next location on the patient that should be probed by the stethoscope bell for storing the lung waveforms into memory.

Controls and Functions

Figure 7A:
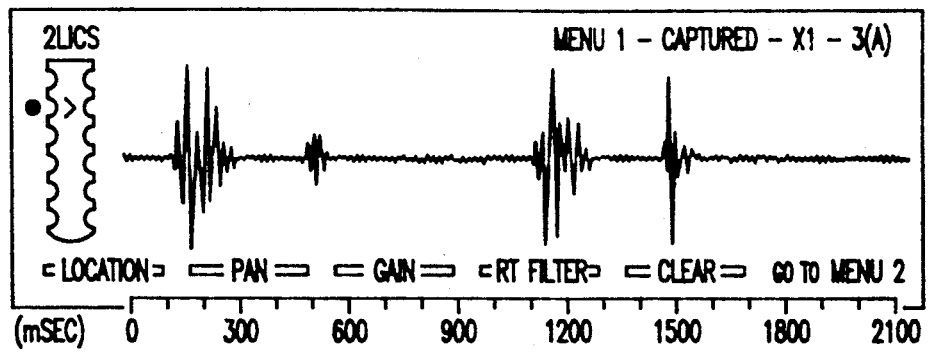
FIG. 7a-7l show the display of the visual display stethoscope showing the various information displayed when certain of the menu keys are depressed.
Figure 7B:
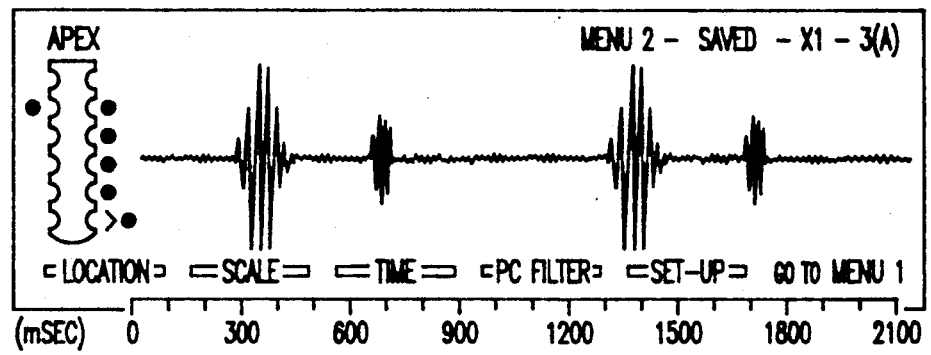

The functions of the visual display stethoscope of the present invention are presented on two menu screens shown in FIGS. 7a and 7b. The MENU 1 display is shown in FIG. 7a, and the MENU 2 display is shown in FIG. 7b. All MENU 1 functions are used for real time waveform observation and manipulation prior to saving the waveform in memory. All MENU 2 functions are used for analysis of waveforms once they are stored in memory. The following discussion will first describe the functions and the corresponding displays of MENU 1, followed by a discussion of the functions and corresponding displays of MENU 2.

Figure 7C:
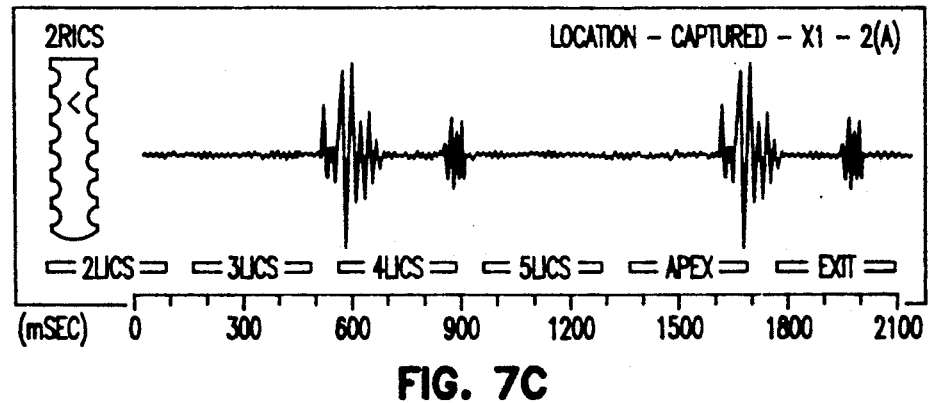

From the MENU 1 screen pressing the LOCATION key changes the screen format to that shown in FIG. 7c. By pressing the appropriate menu key 140-148, the user can select the location on the sternum diagram where the user wants to store a waveform data if saving waveforms, or where to observe data previously saved at that location. The pointer on the sternum diagram automatically moves to the location selected. Also, the selected location is displayed above the sternum diagram (e.g. "APEX" in FIG. 7b). Pressing the EXIT key will cause the screen to revert back to the MENU 1 screen shown in FIG. 7a.

Figure 7D:
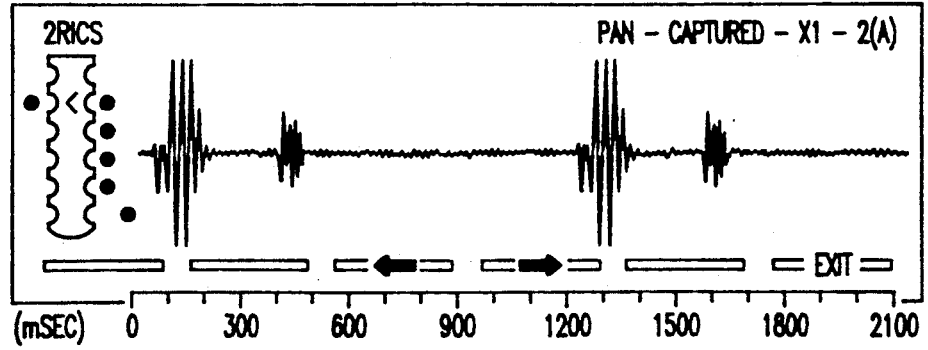

Pressing the PAN key from the MENU 1 screen changes the screen format to that shown in FIG. 7d. Pressing the left arrow key pans the waveform to the right allowing the user to see additional segments of the waveform. Pressing the right arrow key pans the waveform to the left allowing the user to see additional segments of the waveform. Pressing the EXIT key will cause the screen to revert back to the MENU 1 screen.

Figure 7E:
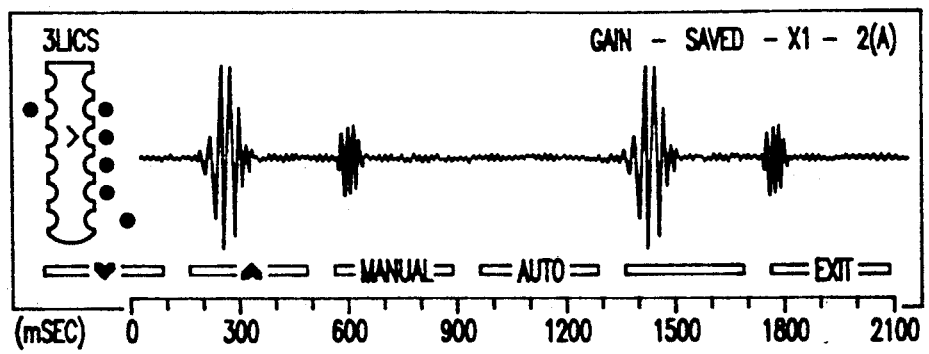

Pressing the GAIN key from the MENU 1 screen changes the screen format to that shown in FIG. 7e. Pressing the MANUAL key, as shown in FIG. 7e, activates the up and down arrows. Pressing the up arrow increases the gain until a maximum of ten is reached. Pressing the down arrow decreases the gain until a minimum of 1 is reached. All waveforms displayed will be amplified by the set gain while in the manual mode. The gain can be adjusted up or down while obtaining real time waveforms. Any change will occur at the end of the current sweep.

Pressing the AUTO key places the GAIN function into auto mode. In this mode the waveform is amplified as necessary to present a full waveform on the display screen.

Figure 7F:
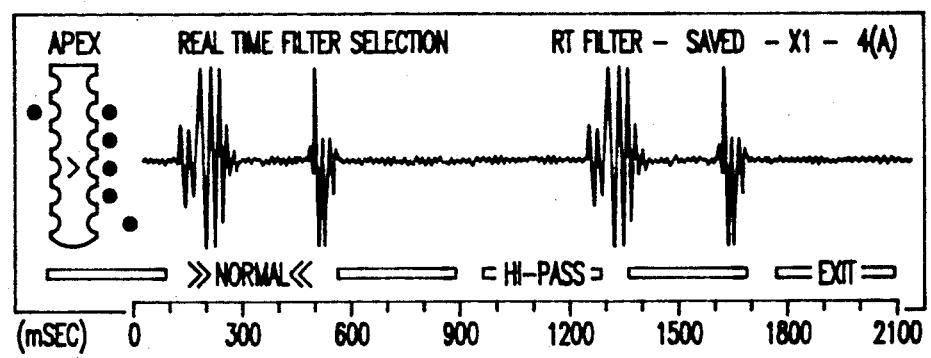

Pressing the RT FILTER key from the Menu 1 screen changes the screen format to that shown in FIG. 7f. This function can be used to obtain real-time filtering of the displayed body sounds for better visualization of high frequency murmurs such as aortic insufficiency. The real time filtering is accomplished using the analog filter circuit shown in FIG. 3f and 3g. Pressing NORMAL selects a filter with a band pass from about 50 hz to 500 hz. Pressing HI-PASS selects a filter with a band pass from about 200 hz to 500 hz. The high pass filter filters out low frequency components of the displayed body sounds, thus allowing better visualization of high frequency murmurs such as aortic insufficiency.

Filter selection can be made while obtaining real time waveforms. The filter option selected will occur at the end of the current sweep. Note in FIG. 7f that the filter option selected is denoted by arrow markers, for example >>NORMAL<<.

Figure 7G:
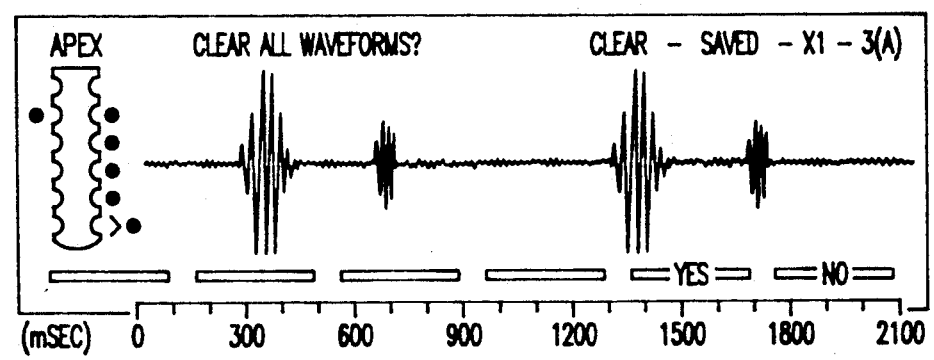

Pressing the CLEAR key from the MENU 1 screen changes the screen format to that shown in FIG. 7g. Pressing the YES key causes the six memory locations to be cleared of all waveform data. Pressing the NO key cancels the clear function. Pressing the GO TO MENU 2 key from the MENU 1 screen causes the MENU 2 screen to be displayed, as shown in FIG. 7b. The MENU 2 functions and displays will now be explained.

The LOCATION key on the MENU 2 screen performs the exact same function as the LOCATION key on the MENU 1 screen.

Figure 7H:
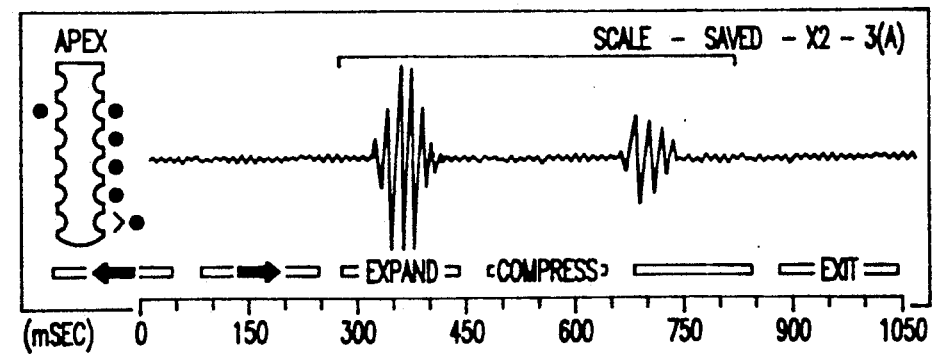

Pressing the SCALE key from the MENU 2 screen changes the screen format to that shown in FIG. 7h. The arrow keys allow the bracket to be moved to any part of the displayed waveform which the user would like to expand or contract. Pressing the EXPAND key expands the time base of the bracketed segment of the waveform by 2x. Pressing the EXPAND key again expands the time base to 4x. Pressing the COMPRESS key causes the time base to compress by 2x each time the key is pressed until the waveform is at its 1x time base.

Figure 7I:
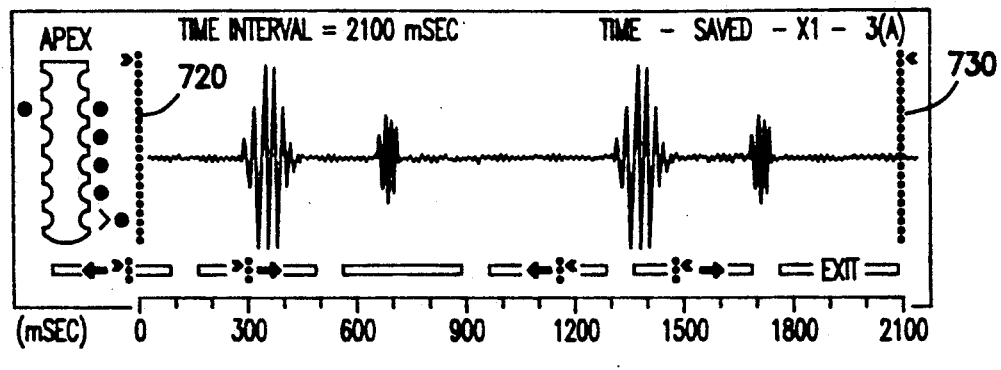

Pressing the TIME key from the MENU 2 screen changes the screen format to that shown in FIG. 7i. This function gives the user the ability to perform specific interval timing on strategic valvular events to aid in the identification of abnormalities. Pressing the left cursor left and right arrow keys moves the left cursor 720 to the left or right, respectively. Pressing the right cursor left and right arrow keys moves the right cursor 730 to the left or right, respectively.

Moving the cursors allows precise time interval measurements of displayed waveforms. The time interval displayed on the screen is the interval between the two cursors (e.g , TIME INTERVAL=2,100 mSec). It should be noted that the TIME function can be used in conjunction with the SCALE function for more precise time measurements. The software flowchart for implementing the TIME function is shown in FIG. 4d and described above in the associated portion of the Detailed Description.

Figure 7J:
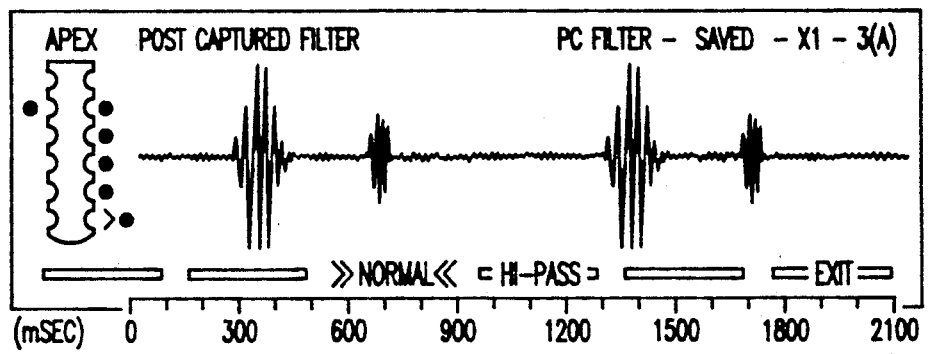

Pressing the PC FILTER key from the MENU 2 screen changes the screen format to that shown in FIG. 7j. Pressing HI-PASS causes the displayed waveform to be filtered in a postcapture digital technique through a band pass of about 200 hz to 500 hz. The preferred embodiment of the present invention utilizes a 16 tap finite impulse response (FIR) linear phase digital filter to accomplish this band pass filtering. The HI-PASS filter function filters out low frequency components of the displayed waveform, thus allowing better visualization of high frequency murmurs. Pressing NORMAL allows the user to see the waveform as it was prior to high pass filtering, with displayed frequencies of about 50 hz to 500 hz. The software flowchart for implementing the PC FILTER function is shown in FIG. 4e and described above in the associated portion of the Detailed Description.

Figure 7K:
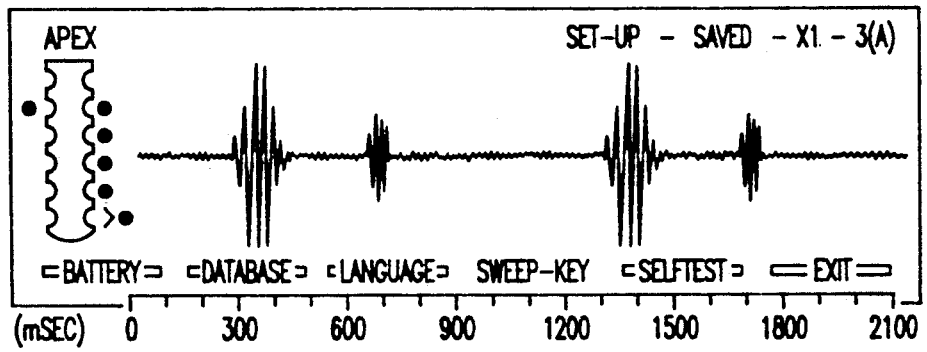
Figure 7L:
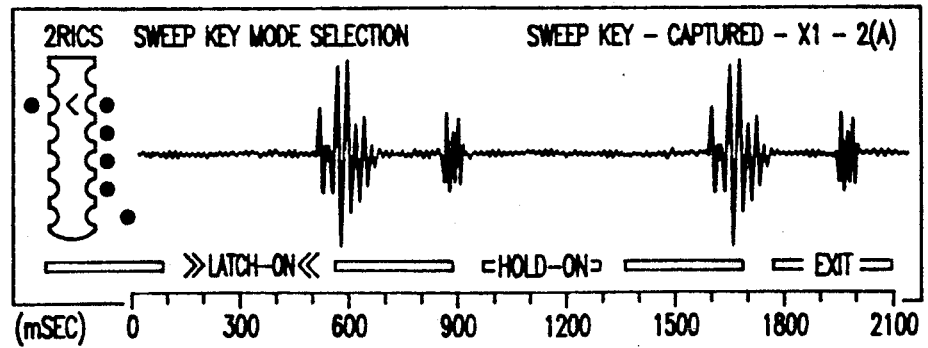
Figure 8A:
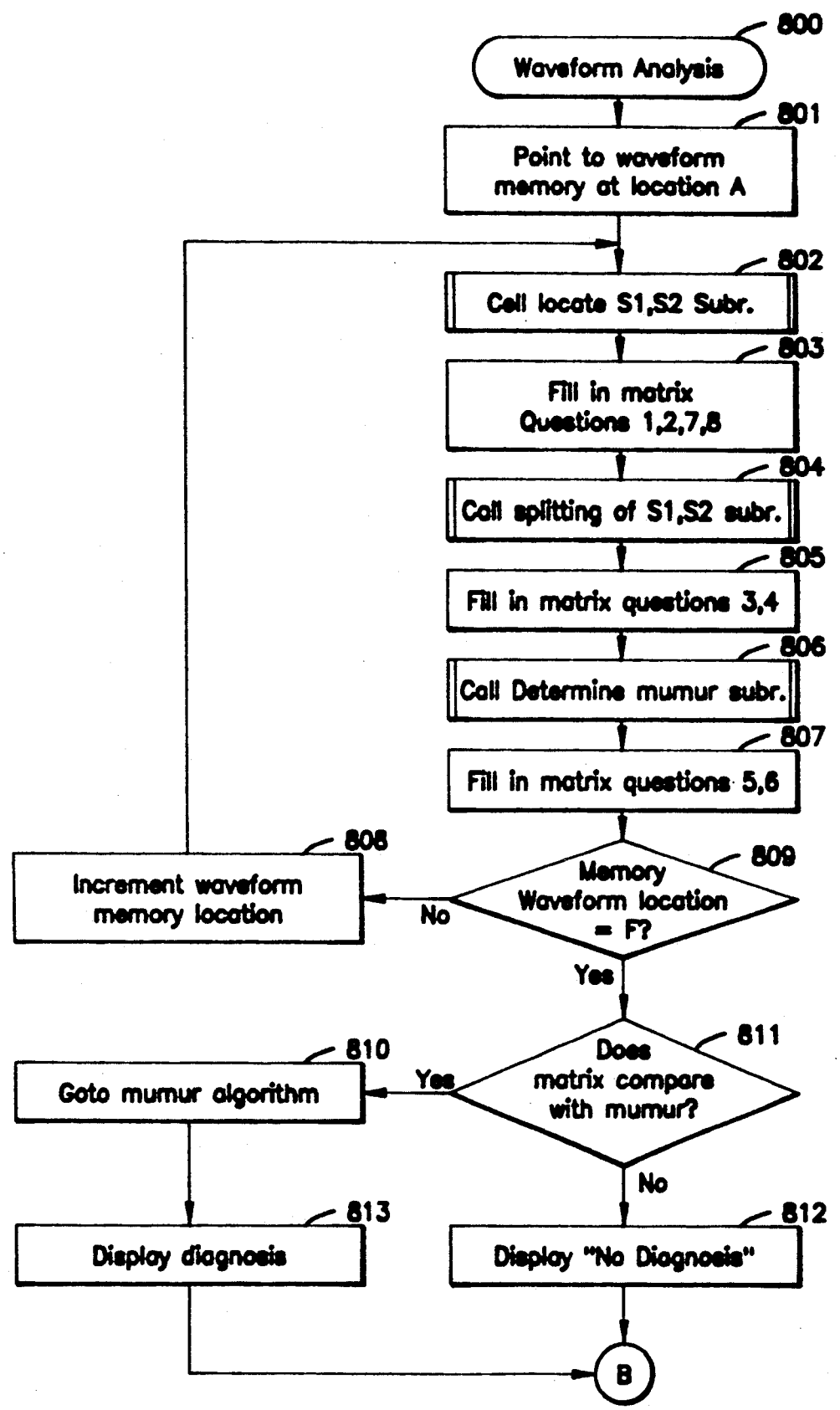
Figure 8C:
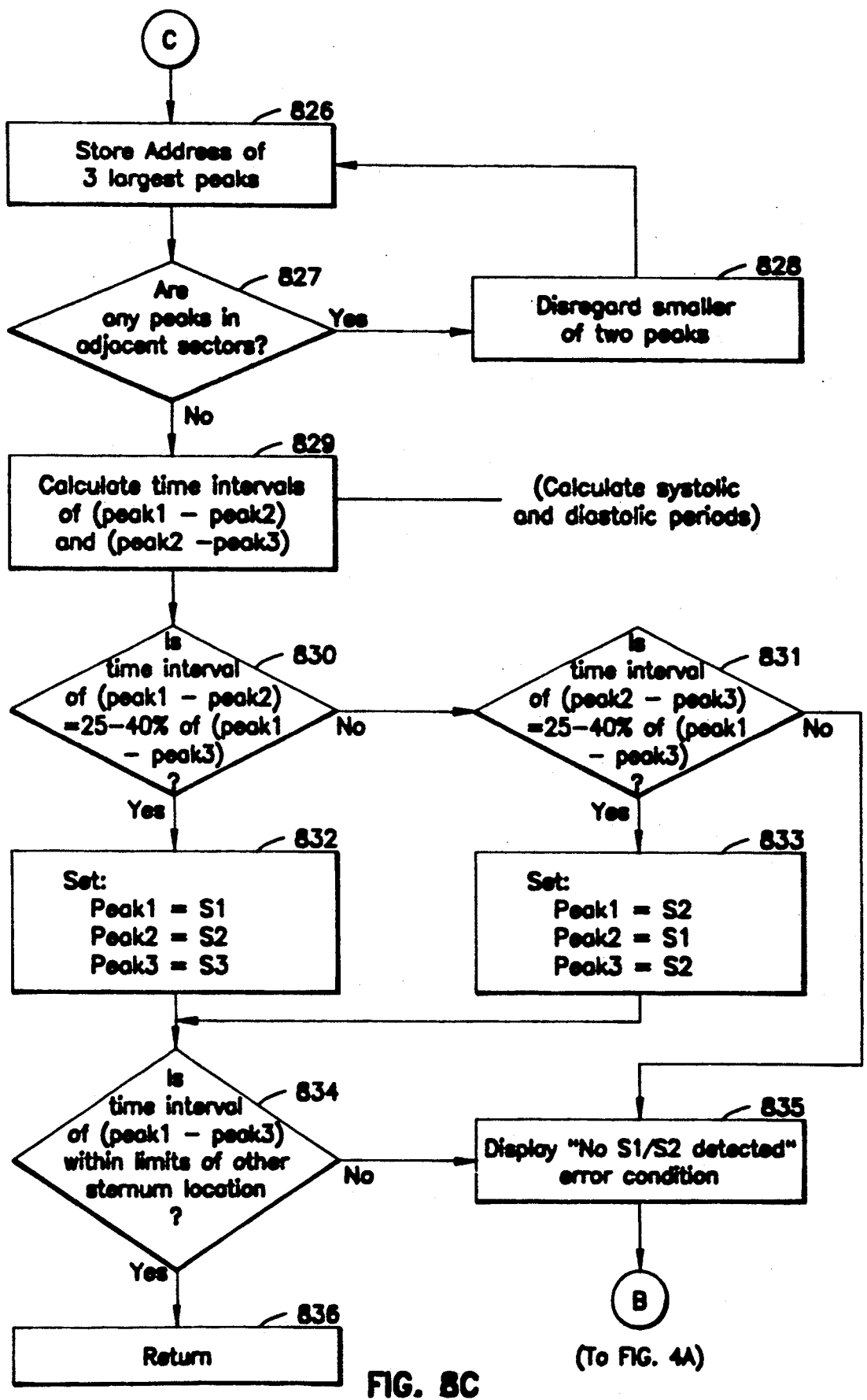
Figure 8D:
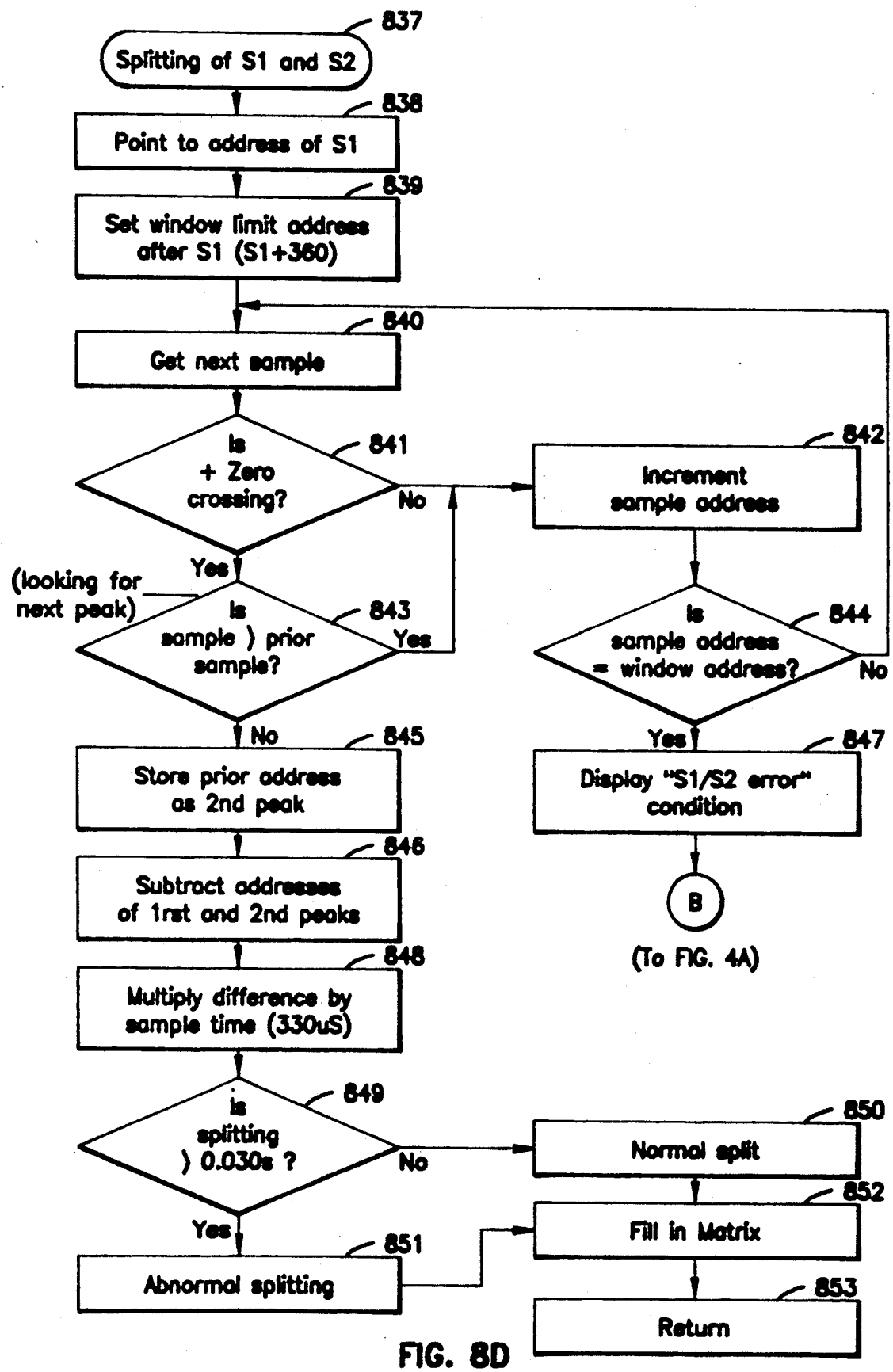
Figure 8E:
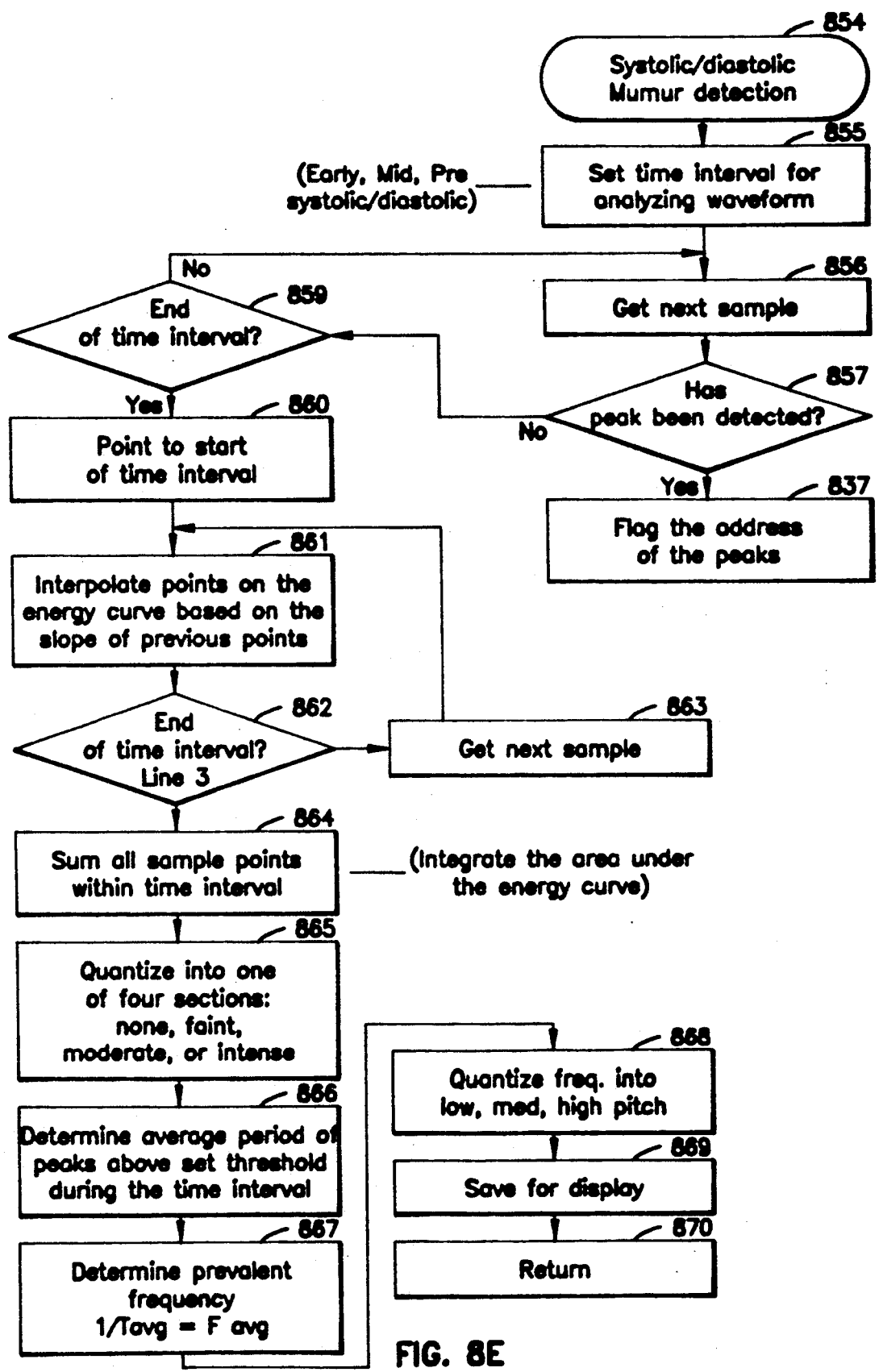
Figure 8F:
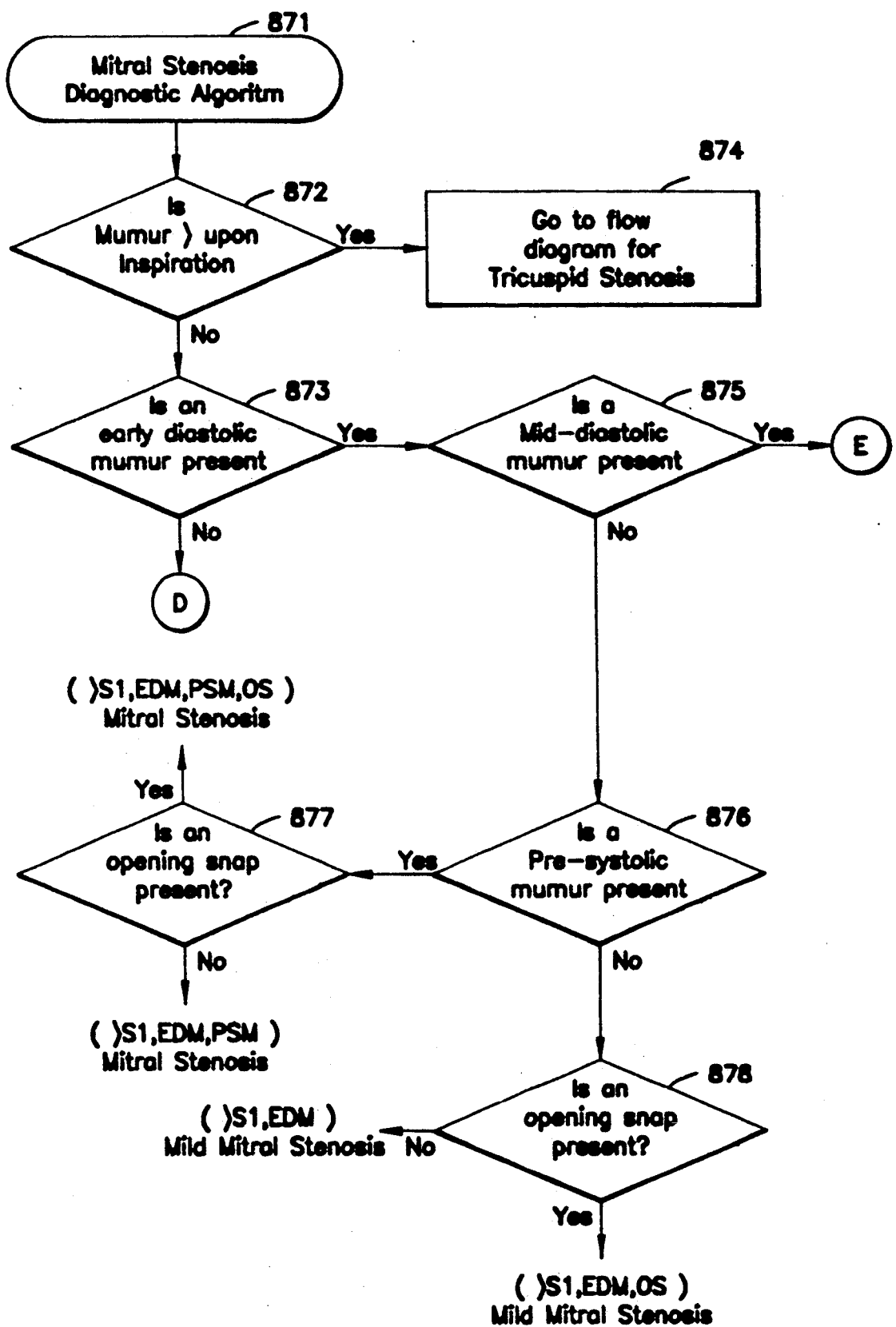
Figure 8G:
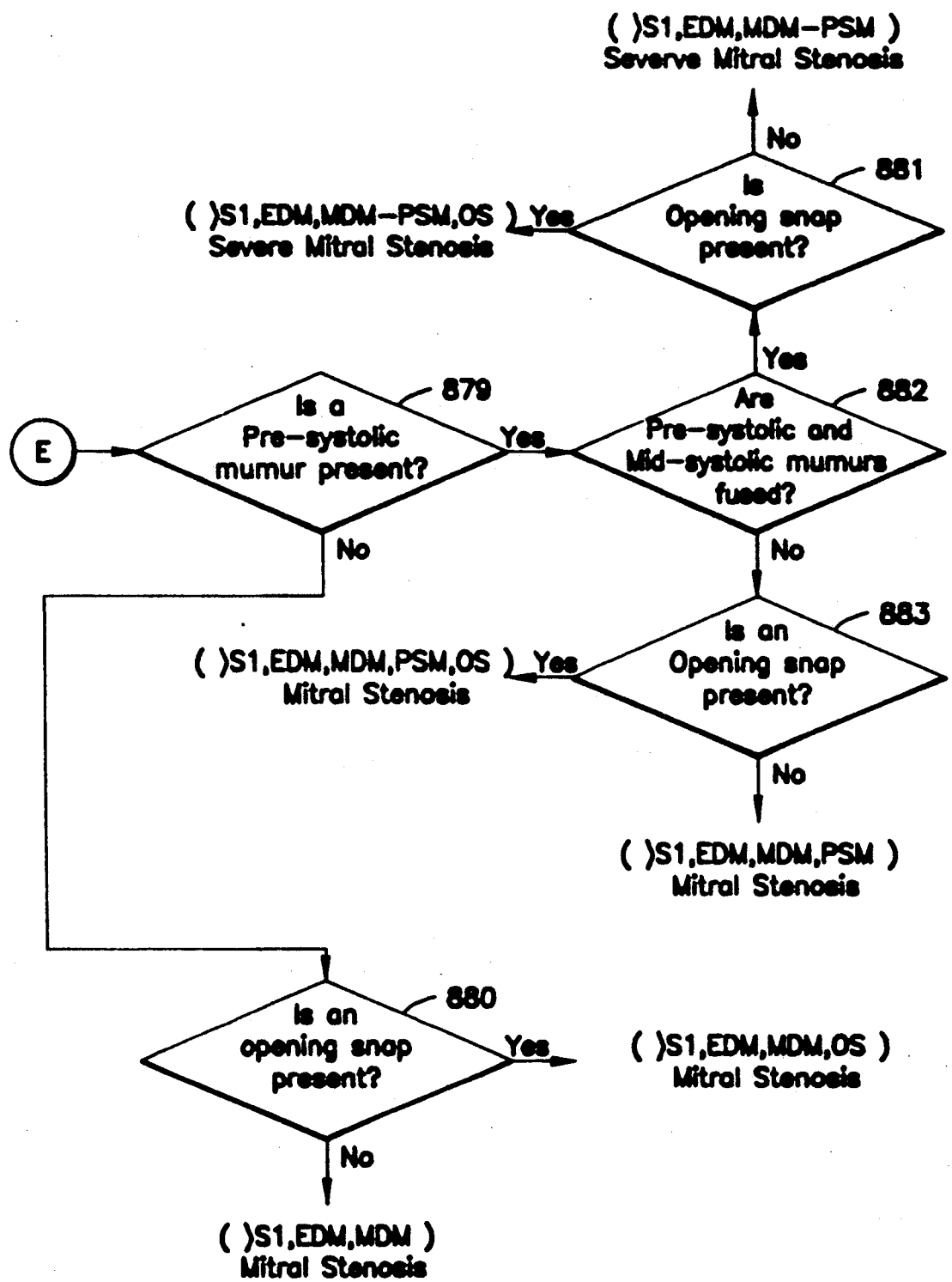
Figure 8H:
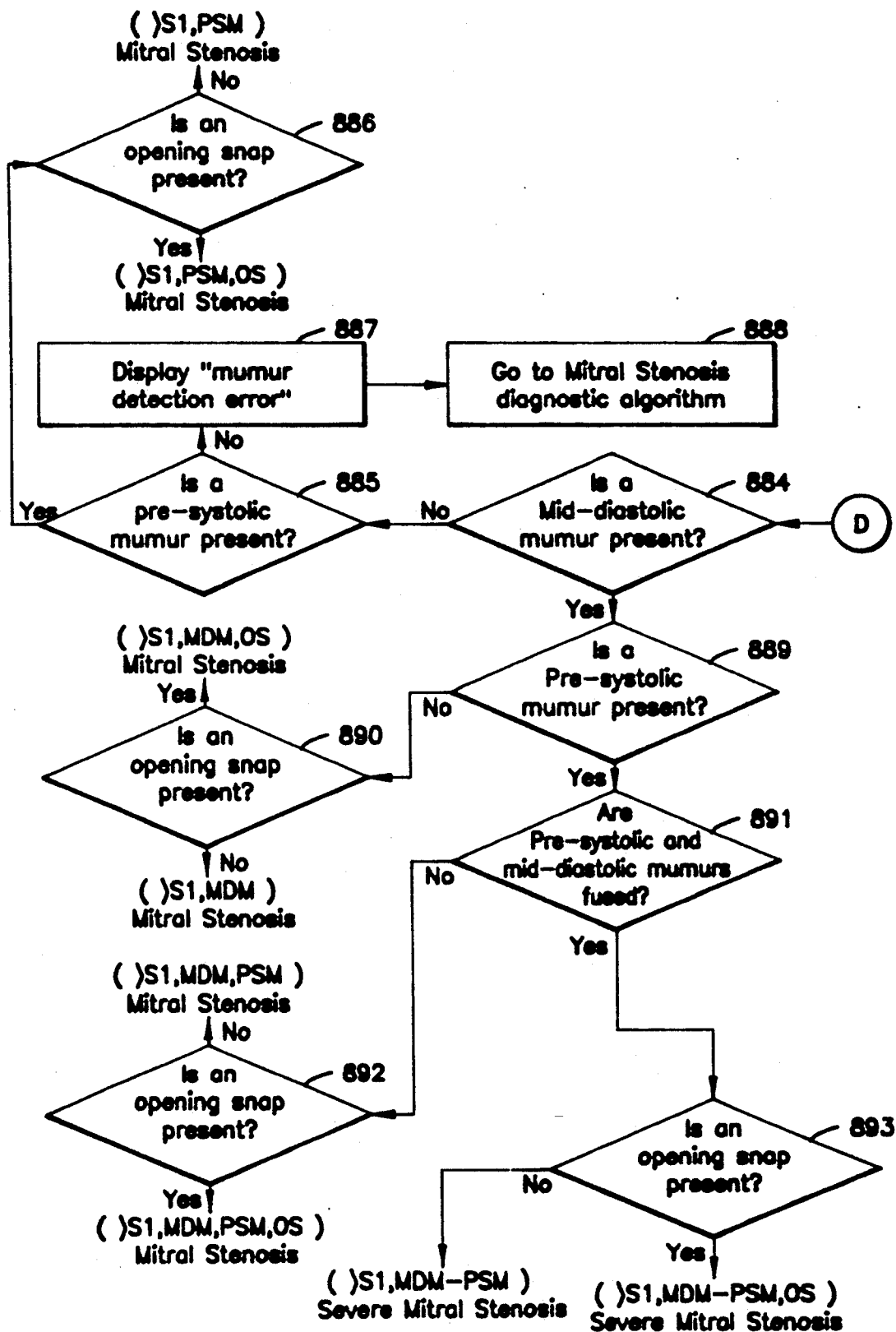
Figure 10:
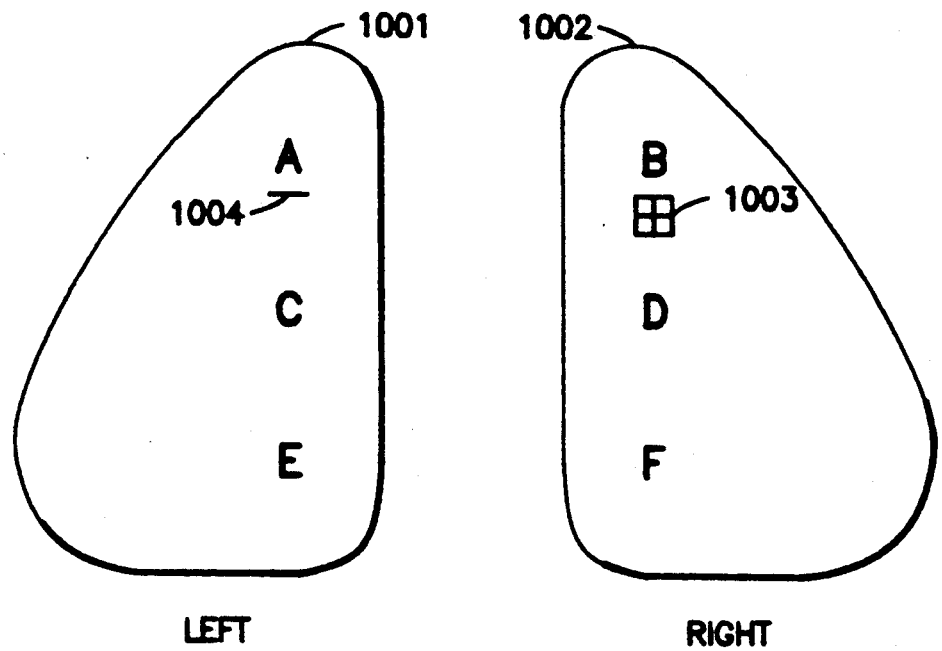
Figures 11A, 11B, 12:
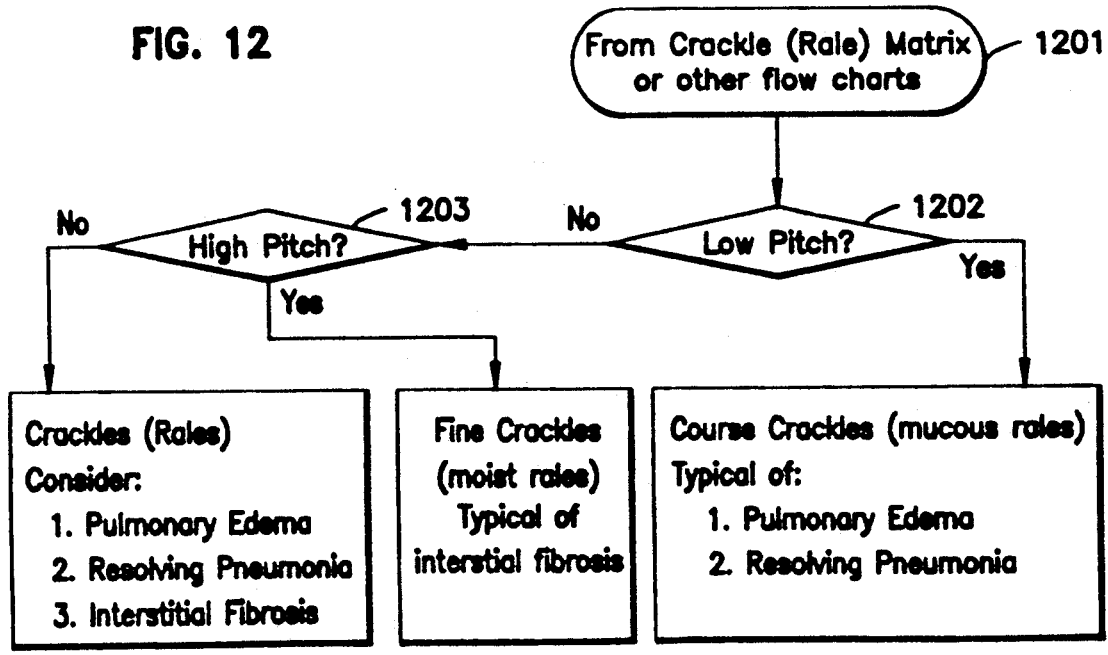
Figure 13:
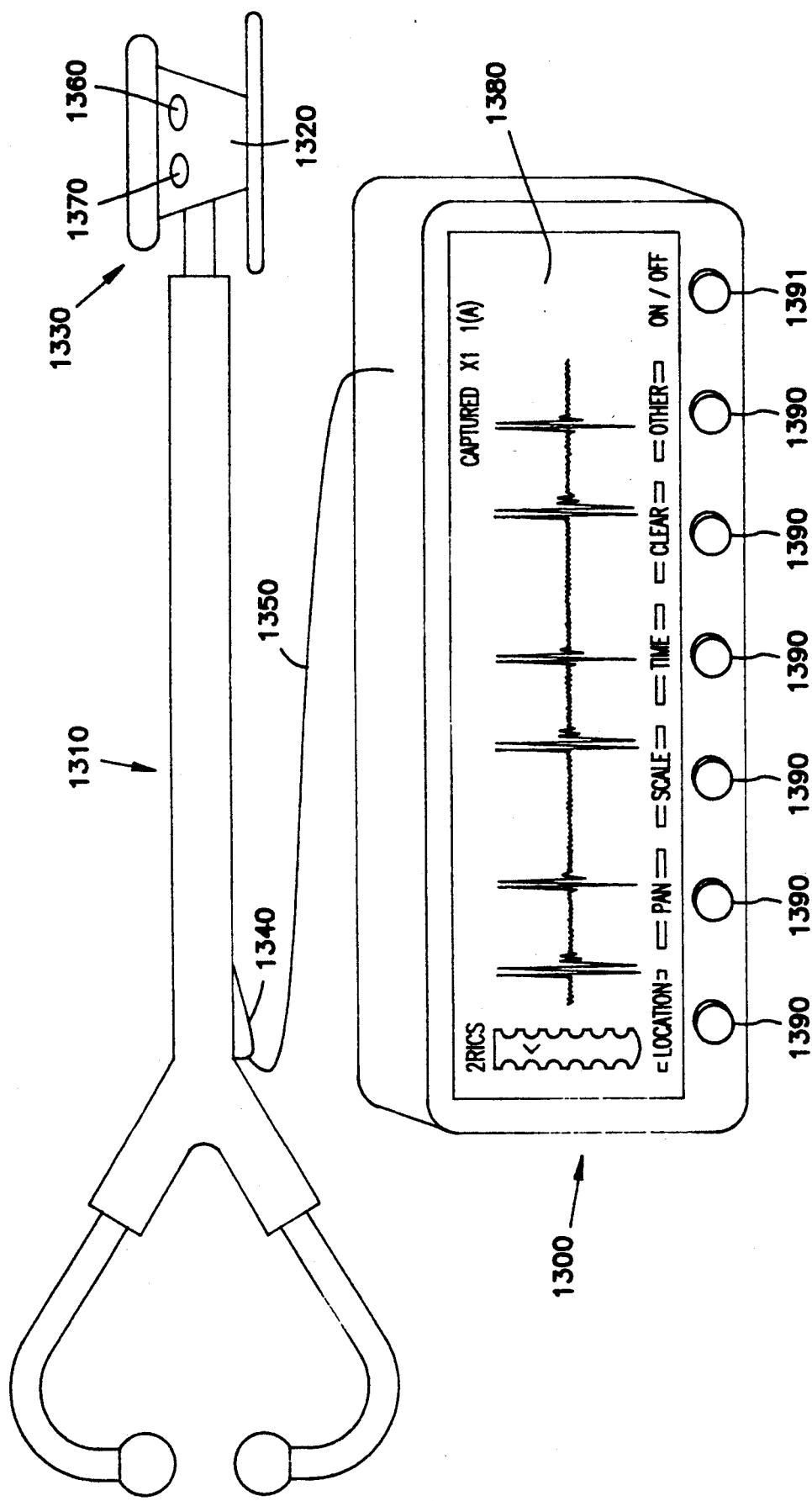
Figure 14A:
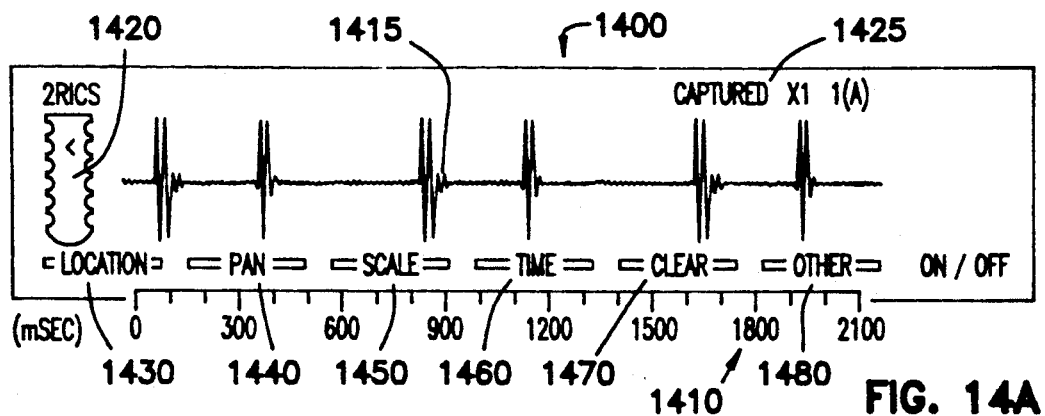
Figure 14B:
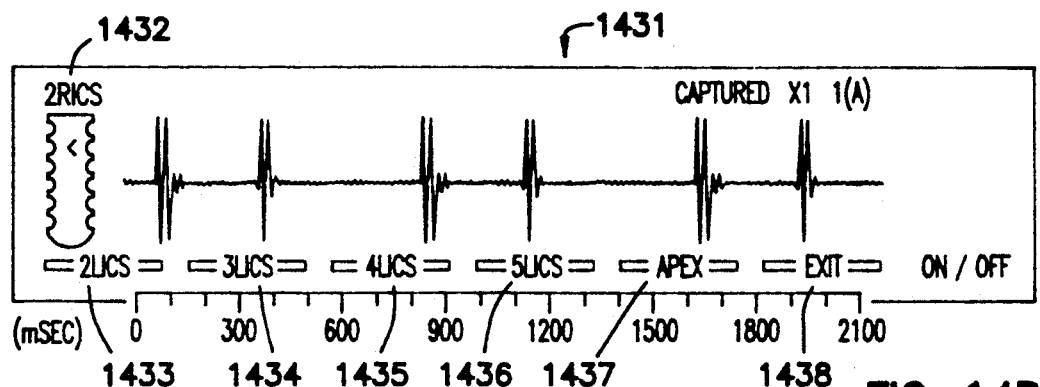
Figure 14C:
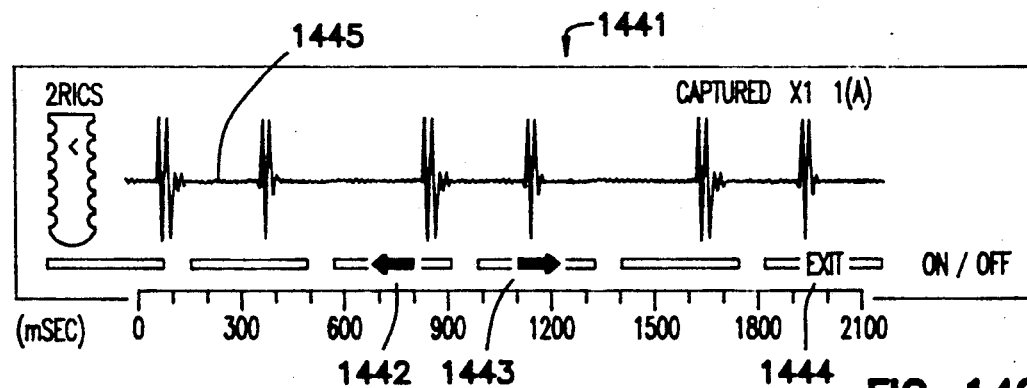
Figure 14D:
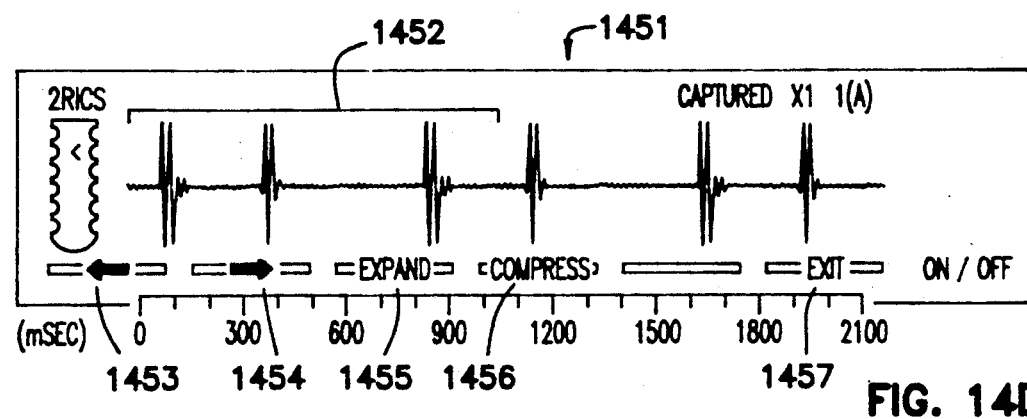
Figure 14E:
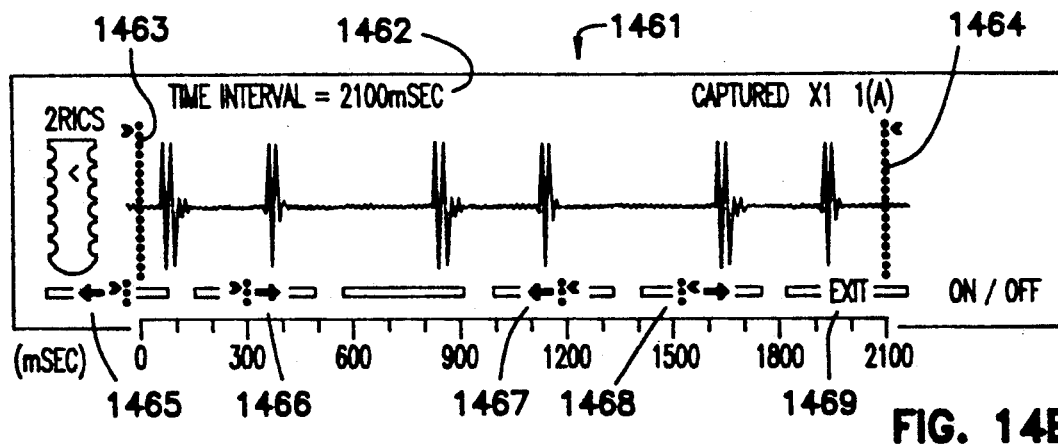
Figure 14F:
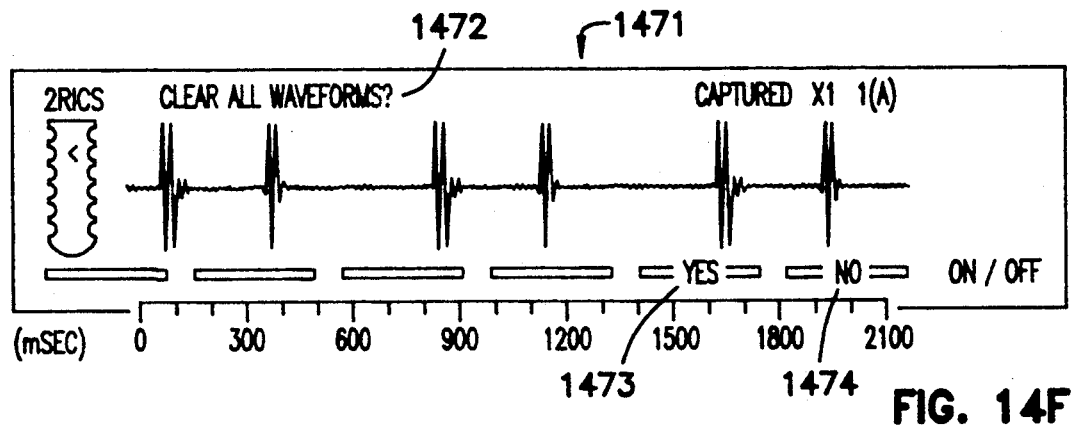
Figure 14G:
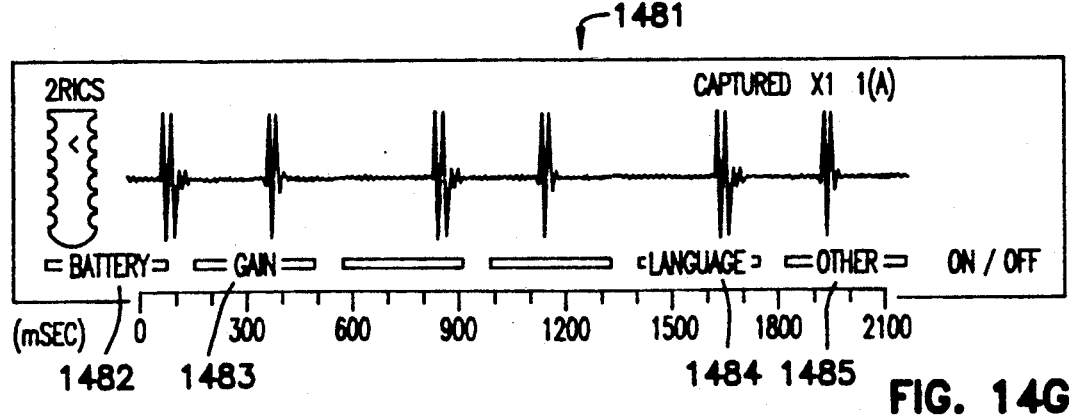
Figure 14H:
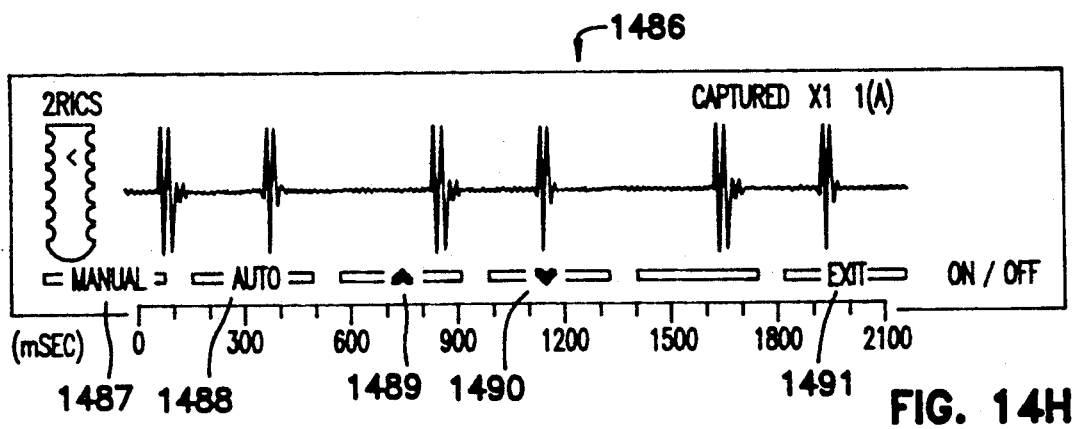
Figure 14I:
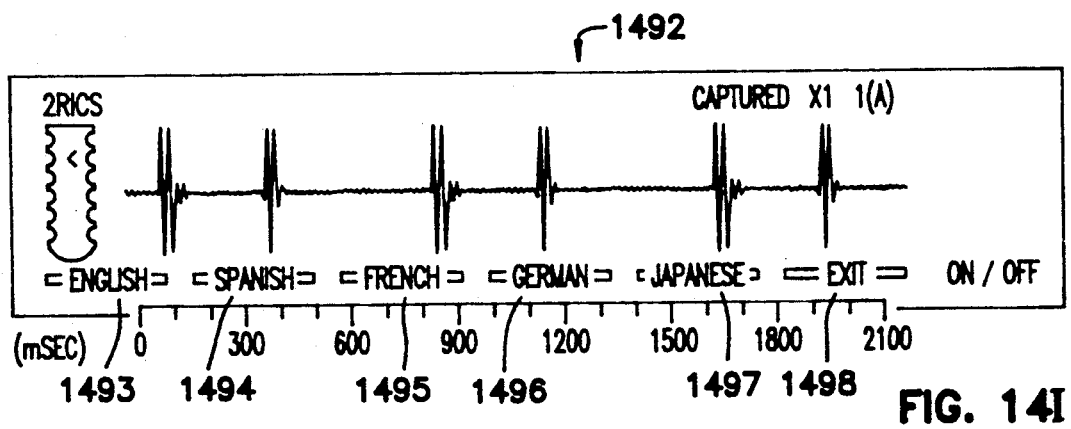

Pressing the SET-UP key from the MENU 2 screen changes the screen format to that shown in FIG. 7k. Pressing the BATTERY key causes the display to show the battery status. Pressing the SWEEP-KEY from the display shown in FIG. 7k, changes the screen format to that shown in FIG. 7l. Pressing the LATCH-ON key causes the sweep switch to operate like a stopwatch. Push once to start the sweep and push again to stop sweep and capture the waveform.

Pressing the HOLD-ON key causes the sweep switch to operate only when being pressed. Pushing and holding the sweep switch causes a sweep, releasing the sweep switch terminates the sweep and captures the waveform.

Referring again to FIG. 7k, pressing the DATA BASE key allows the user to download data from the stethoscope to a peripheral device, such as a PC or Printer, or allows the user to download the data from a peripheral device to the visual display stethoscope.

Pressing the SELF-TEST key causes the visual display stethoscope of the present invention to undergo an automatic self-testing procedure for the detection of hardware failures. Pressing the LANGUAGE key allows the visual display stethoscope to be programed in any of several languages, including English, Spanish, French, German and Japanese.

It will be readily apparent to those skilled in the art that many modifications to the preferred embodiment of the present invention are possible without deviating from the scope and spirit of the present invention. Special conditions employed for the implementation of the preferred embodiment are not intended to be limiting and are easily adaptable to alternate implementations. For example, the control structure of the present invention is generally implemented using microprocessor-based architectures and logic functions. It will be readily understood by those skilled in the art upon reading and understanding this specification and drawings that the control structure of the present invention may be implemented in a wide variety of different ways, including the use of external computer control, ROM microcode control, PLA or PAL logic structures, and other types of hardwired or software controlled state machines. Also, although an LCD display is described, a wide variety of displays could be used such as LED fluorescent, CRT, gas-discharge and others. A microphone is also preferred for receiving the heart sounds although many forms of transducers are acceptable such as direct pressure sensing, mechanical movement sensing, fluid flow sensing, and others.

Although specific software configurations and flow diagrams have been illustrated and described for the preferred embodiment of the present invention set forth herein, it will be appreciated by those of ordinary skill in the art that a wide variety of software implementations calculated to achieve the same purpose may be substituted for the specific software descriptions shown. Thus, although conventional subroutines, decisions and control flow have been described, those skilled in the art will readily recognize the substitution of a wide variety of alternate control flows, interrupt-driven routines, external control mechanisms, and the use of hardware control as opposed to software control without deviating from the spirit and scope of the present invention. Those experienced in the electrical and computer arts will readily recognize that the present invention may be implemented in a very wide variety of embodiments.

While the present invention has been described in connection with a preferred embodiment thereof, it will be understood that many modifications will be readily apparent to those of ordinary skill in the art, and this application is intended to cover any adaptations or variations thereof. Therefore, it is manifestly intended that this invention be limited only by the claims and the equivalents thereof.

I claim:

1. A visual display stethoscope adapted to receive and display body sounds from a plurality of body locations for use by an operator, comprising;
    transducer means for receiving the body sounds from the plurality of body locations, and for converting each of the plurality of body sounds into an electrical signal;
    memory means operatively coupled to said transducer means for storing said electrical signals for each of the plurality of body locations;
    display means operatively coupled to said memory means for receiving said electrical signal for a selected one of the plurality of body locations and for displaying a visual representation of said electrical signal;
    means, coupled to a control means, for allowing the operator to identify a first location on said visual representation of said electrical signal and for allowing the operator to identify a second location on said visual representation of said displayed electrical signal; and
    said control means for measuring the time interval between said first location on said electrical signal and said second location on said electrical signal and for displaying on said display means measurements therefrom.

2. The stethoscope according to claim 1 further comprising an acoustic input and an acoustic output acoustically connected to said acoustic input, wherein said transducer is interfaced with said acoustic input.

3. The stethoscope according to claim 1 wherein said control means further comprises means operatively coupled to said memory means for associating each said electrical signal with a corresponding one of said plurality of body locations; and
    wherein said display means further includes indicator means on a sternum diagram for associating at least one said electrical signal with said selected one of said body locations on said diagram.

4. The stethoscope according to claim 1 wherein said visual representation of said electrical signal is a waveform and wherein said body sounds are heart sounds.

5. The stethoscope according to claim 1 wherein said control means further includes means for displaying written language on said display means.

6. The stethoscope according to claim 1 wherein said transducer means and said display means are operatively coupled but are in different modules.

7. A visual display stethoscope adapted to receive and display body sounds from a plurality of body locations for use by an operator, comprising:
   microphone means for receiving said body sounds from said plurality of body locations, and for converting each of said body sounds into an analog electrical signal;
   analog-to-digital convertor means operatively coupled to said microphone means for converting said analog electrical signal into a digital electrical signal;
   memory means operatively coupled to said convertor means for storing a portion of said digital electrical signal for each of said plurality of body locations;
   display means operatively coupled to said memory means for receiving said digital electrical signal for a selected one of said plurality of body locations and displaying a visual representation of said digital electrical signal for said selected one of said body locations;
   keypad means, operatively coupled to a control means, for receiving commands from the operator;
   cursor means, operatively coupled to said control means for allowing the operator to identify a first location on said visual representation of said electrical signal and for allowing the operator to identify a second location on said visual representation of said displayed electrical signal; and
   said control means connected to said memory means for measuring a time interval between said first location on said visual representation of said electrical signal and said second location on said visual representation said electrical signal.

8. The stethoscope according to claim 7, wherein said control means is further adapted for displaying on said display means the measurement of said time interval.

9. The stethoscope according to claim 7 further comprising an acoustic input and an acoustic output acoustically connected to said acoustic input, wherein said microphone means is interfaced with said acoustic input.

10. The stethoscope according to claim 7 wherein said control means further comprises means operatively coupled to said memory means for associating each said digital electrical signal with a corresponding one of said plurality of body locations; and
   wherein said means further includes indicator means on said display means for associating said visual representation of said digital electrical signal with said selected one of said body locations.

11. The stethoscope according to claim 8 wherein said visual representation of said electrical signal is a waveform and said body sounds are heart sounds.

12. The stethoscope according to claim 7 wherein said control means further includes means for displaying written language on said display means.

13. The stethoscope according to claim 7 wherein said microphone means and said display means are operatively coupled but are in different modules of the stethoscope.

14. A visual display stethoscope adapted to receive and display body sounds from a plurality of body locations for use by an operator, comprising;
   transducer means for receiving the body sounds from the plurality of body locations, and for converting each of the plurality of body sounds into an electrical signal;
   memory means operatively coupled to said transducer means for storing said electrical signals for each of the plurality of body locations;
   display means operatively coupled to said memory means for receiving said electrical signal for a selected one of the plurality of body locations and for displaying a visual representation of said electrical signal;
   filter means operatively coupled to receive said electrical signal for filtering said electrical signal through one of a plurality of band pass filters;
   selection means connected to said filter means for allowing the operator to select between said plurality of band pass filters and for producing therefrom a filtered electrical signal; and
   said display means further adapted for displaying a visual representation of said filtered electrical signal.

15. The stethoscope according to claim 14 wherein said filter means is coupled to said transducer means and further includes analog filter means for filtering said electrical signal.

16. The stethoscope according to claim 14 wherein said filter means further is coupled to said memory means and further includes digital filter means for filtering said electrical signal.

17. The stethoscope according to claim 14 wherein said filter means is coupled to said transducer means and further includes digital filter means for filtering said electrical signal.

18. The stethoscope according to claim 14 wherein said filter means further is coupled to said memory means and further includes analog filter means for filtering said electrical signal.

19. The stethoscope according to claim 14 further comprising an acoustic input and an acoustic output acoustically connected to said acoustic input, wherein said transducer is interfaced with said acoustic input.

20. The stethoscope according to claim 14 further including a control means, operatively coupled to said memory means, for associating each said electrical signal with a corresponding one of said plurality of body locations; and
   wherein said display means further includes indicator means on a diagram for associating at least one said electrical signal with said selected one of said body locations on said diagram.

21. The stethoscope according to claim 14 wherein said visual representation of said electrical signal is a waveform and wherein said body sounds are heart sounds.

22. The stethoscope according to claim 14 wherein said transducer means and said display means are operatively coupled but are in different modules.

23. A visual display stethoscope adapted to receive and display body sounds from a plurality of body locations for use by an operator, comprising:
   microphone means for receiving said body sounds from said plurality of body locations, and for converting each of said body sounds into an analog electrical signal;

analog-to-digital convertor means operatively coupled to said microphone means for converting said analog electrical signal into a digital electrical signal;

memory means operatively coupled to said convertor means for storing a portion of said digital electrical signal for each of said plurality of body locations;

display means operatively coupled to said memory means for receiving said digital electrical signal for a selected one of said plurality of body locations and displaying a visual representation of said digital electrical signal for said selected one of said body locations;

keypad means, operatively coupled to a control means, for receiving commands from the operator;

filter means operatively coupled to receive said electrical signal through one of a plurality of band pass filters;

selection means connected to said filter means for allowing the operator to select between said plurality of band pass filters and for producing therefrom a filtered electrical signal; and said display means further adapted for displaying a visual representation of said filtered electrical signal.

24. The stethoscope according to claim 23, wherein said filter means is coupled to said microphone means and further includes analog filter means for filtering said electrical signal.

25. The stethoscope according to claim 23 wherein said filter means is coupled to said memory means and further includes digital filter means for filtering said electrical signal.

26. The stethoscope according to claim 23 further comprising an acoustic input and an acoustic output acoustically connected to said acoustic input, wherein said microphone means is interfaced with said acoustic input.

27. The stethoscope according to claim 23 wherein said control means further comprises means operatively coupled to said memory means for associating each said digital electrical signal with a corresponding one of said plurality of body locations; and wherein said means further includes indicator means on said display means for associating said visual representation of said digital electrical signal with said selected one of said body locations.

28. The stethoscope according to claim 23 wherein said visual representation of said electrical signal is a waveform and said body sounds are heart sounds.

29. The stethoscope according to claim 23 wherein said control means further includes means for displaying written language on said display means.

30. The stethoscope according to claim 23 wherein said microphone means and said display means are operatively coupled but are in different modules of the stethoscope.

31. A method of operating a visual display stethoscope adapted to receive and display body sounds for use by an operator, comprising the steps of:
receiving the body sounds;
converting the of body sounds into an electrical signal;
storing said electrical signal;
displaying a visual representation of said electrical signal;

receiving operator selected locations for at least two locations on said electrical signal;
measuring a time interval between said operator selected locations and producing therefrom a measurement; and
displaying said measurement.

32. A method of operating a visual display stethoscope adapted to receive and display body sounds for use by an operator, comprising the steps of:
receiving the body sounds;
converting the body sounds into an electrical signal;
storing said electrical signal;
displaying a visual representation of said electrical signal;
filtering said electrical signal through one of a plurality of band pass filtersand producing therefrom a filtered electrical signal; and
displaying a visual representation of said filtered electrical signal.

33. A method according to claim 32 further including the step of receiving an operator selected choice of one of the plurality of band pass filters.

34. A visual display stethoscope adapted to receive and display body sounds from a plurality of body locations for use by an operator, comprising;
a transducer adapted to receive the body sounds from the plurality of body locations, said transducer converting each of the plurality of body sounds into an electrical signal;
a memory operatively coupled to said transducer, said memory capable of storing said electrical signals for each of the plurality of body locations;
a display operatively coupled to said memory and adapted to receive said electrical signal for a selected one of the plurality of body locations and to display a visual representation of said electrical signal;
a keypad, operatively coupled to a controller, said keypad adapted to receive commands from the operator;
a plurality of cursors on said display and controlled by said controller, and adapted for allowing the operator to identify a first location on said visual representation of said electrical signal and for allowing the operator to identify a second location on said visual representation of said displayed electrical signal; and
said controller adapted to measure the time interval between said first location on said electrical signal and said second location on said electrical signal and to display on said display measurements therefrom.

35. A visual display stethoscope adapted to receive and display body sounds from a plurality of body locations for use by an operator, comprising:
a transducer adapted to receive said body sounds from said plurality of body locations, said transducer converting each of said body sounds into an analog electrical signal;
an analog-to-digital convertor operatively coupled to said transducer adapted to convert said analog electrical signal into a digital electrical signal;
a memory operatively coupled to said convertor adapted to store a portion of said digital electrical signal for each of said plurality of body locations;
a display operatively coupled to said memory adapted to receive said digital electrical signal for a selected one of said plurality of body locations and to display a visual representation of said digital electrical signal for said selected one of said body locations;

a plurality of band pass filters operatively coupled to receive said electrical signal;

a keypad connected to said plurality of band pass filters adapted to receive an operator selected choice between said plurality of band pass filters and for producing therefrom a filtered electrical signal; and said display further adapted to display a visual representation of said filtered electrical signal.

* * * * *

UNITED STATES PATENT AND TRADEMARK OFFICE
CERTIFICATE OF CORRECTION

PATENT NO. : 5,213,108

DATED : May 25, 1993

INVENTOR(S) : Mark S. Bredesen et al.

It is certified that error appears in the above-identified patent and that said Letters Patent is hereby corrected as shown below:

Title Page:
　　In the Abstract, line 1, "An" should read --A-- therefore.

In column 5, line 58, insert --dedicated key which is configured as shown on the power-- after the letter "a".

In column 6, line 30, insert --on-- after the word "indicated" therefore.

In columns 7 and 8, lines 27 and 6 respectively, "2KHz" should read --2kHz-- therefore.

In column 7, line 34, "200hz" should read --200Hz-- therefore.

In column 8, line 24, "generate" should read --generates-- therefore.

In column 8, lines 41 and 42, "resolution" should read --resolutions-- therefore.

In column 9, line 20, "were" should read --where-- therefore.

In column 9, line 36, "pulled" should read --polled-- therefore.

In column 9, lines 59 and 62, "hz" should read --Hz-- therefore.

UNITED STATES PATENT AND TRADEMARK OFFICE
CERTIFICATE OF CORRECTION

PATENT NO. : 5,213,108

DATED : May 25, 1993

INVENTOR(S) : Mark S. Bredesen et al.

It is certified that error appears in the above-identified patent and that said Letters Patent is hereby corrected as shown below:

In column 14, lines 18, 19 and 20 (twice), "hz" should read --Hz-- therefore.

In column 15, lines 7 (twice) and 16 (twice), "hz" should read --Hz-- therefore.

In column 17, line 43, insert --of-- after the word "representation" therefore.

In column 19, line 64, delete "of" after the word "the" therefore.

In column 20, line 16, "filtersand" should read --filters and-- therefore.

Signed and Sealed this

Thirteenth Day of December, 1994

Attest:

BRUCE LEHMAN

Attesting Officer

Commissioner of Patents and Trademarks